United States Patent
Vuorinen et al.

(10) Patent No.: US 12,043,675 B2
(45) Date of Patent: Jul. 23, 2024

(54) NANOFIBRILLAR CELLULOSE PRODUCT AND A METHOD FOR MANUFACTURING THEREOF

(71) Applicant: UPM-Kymmene Corporation, Helsinki (FI)

(72) Inventors: Tapani Vuorinen, Espoo (FI); Pegah Khanjani, Gothenburg (SE); Thaddeus Maloney, Vantaa (FI); Sara Ceccherini, Espoo (FI); Markus Nuopponen, Helsinki (FI); Kari Luukko, Espoo (FI)

(73) Assignee: UPM-KYMMENE CORPORATION, Helsinki (FI)

( * ) Notice: Subject to any disclaimer, the term of this patent is extended or adjusted under 35 U.S.C. 154(b) by 711 days.

(21) Appl. No.: 17/054,314

(22) PCT Filed: May 13, 2019

(86) PCT No.: PCT/EP2019/062187
§ 371 (c)(1),
(2) Date: Nov. 10, 2020

(87) PCT Pub. No.: WO2019/238327
PCT Pub. Date: Dec. 19, 2019

(65) Prior Publication Data
US 2021/0130500 A1    May 6, 2021

(30) Foreign Application Priority Data
Jun. 13, 2018  (EP) .................................... 18397520

(51) Int. Cl.
| C08B 15/00 | (2006.01) |
| A61K 8/02 | (2006.01) |
| A61K 8/73 | (2006.01) |
| A61L 15/28 | (2006.01) |
| A61L 15/44 | (2006.01) |
| C12N 1/22 | (2006.01) |
| C12N 5/00 | (2006.01) |

(52) U.S. Cl.
CPC .......... *C08B 15/005* (2013.01); *A61K 8/0204* (2013.01); *A61K 8/731* (2013.01); *A61L 15/28* (2013.01); *A61L 15/44* (2013.01); *C12N 1/22* (2013.01); *C12N 5/0068* (2013.01); *C12N 2533/78* (2013.01); *C12N 2537/10* (2013.01)

(58) Field of Classification Search
CPC ....... A61K 8/0204; A61K 8/731; A61L 15/28; A61L 15/44; C12N 1/22; C12N 5/0068; C12N 2533/78; C12N 2537/10; C08B 15/005
See application file for complete search history.

(56) References Cited

U.S. PATENT DOCUMENTS

| 9,248,090 | B2* | 2/2016 | Isogai .................... A61Q 19/00 |
| 9,410,285 | B2* | 8/2016 | Vuorinen ............... D21C 9/007 |
| 9,797,093 | B2* | 10/2017 | Laukkanen ............. C08B 15/00 |
| 10,697,116 | B2* | 6/2020 | Nuopponen ........... D21H 11/18 |
| 10,767,307 | B2* | 9/2020 | Pääkkönen ............. D21C 9/007 |
| 11,274,396 | B2* | 3/2022 | Nuopponen ............. D21D 1/36 |
| 2008/0249486 | A1* | 10/2008 | Effing ..................... A61L 15/60 |
| | | | 604/304 |
| 2012/0308624 | A1* | 12/2012 | Isogai .................... A61K 8/345 |
| | | | 424/401 |
| 2014/0010790 | A1 | 1/2014 | Yliperttula et al. |
| 2014/0053995 | A1 | 2/2014 | Graveson |
| 2016/0122947 | A1* | 5/2016 | Kajanto ................. D21H 11/18 |
| | | | 162/146 |
| 2017/0258852 | A1 | 9/2017 | Ma et al. |
| 2018/0021473 | A1 | 1/2018 | Yliperttula et al. |
| 2018/0094081 | A1 | 4/2018 | Nuopponen |

FOREIGN PATENT DOCUMENTS

| EP | 2371893 A1 | 10/2011 |
| EP | 3187195 A1 | 7/2017 |
| EP | 3581591 A1 | 12/2019 |
| WO | 2012120073 A1 | 9/2012 |

OTHER PUBLICATIONS

Jingjing Yao et al., "Macrofibers with High Mechanical Performance Based on Aligned Bacterial Cellulose Nanofibers", ACS Applied Materials & Interfaces, vol. 9, No. 24, Jan. 12, 2017, pp. 20330-20339. (Year: 2017).*
Jowkarderis et al. "Rheology of semi-dilute suspensions of carboxylated cellulose nanofibrils" in Carbohydrate Polymers, 123, 2015, pp. 416-423. (Year: 2015).*
Saito, T. et al., "Cellulose Nanofibers Prepared by TEMPO-Mediated Oxidation of Native Cellulose", American Chemical Society; Published on Web: Jul. 13, 2007; 7 pages.
International Search Report for the corresponding International Application No. PCT/EP2019/062187; International Filing Date: May 13, 2019; Date of Mailing: Aug. 1, 2019; 5 pages.
Kafy, A. et al.: "Cellulose long fibers fabricated from cellulose nanofibers and its strong and tough characteristics", Scientific Reports, vol. 7, No. 17683, 2017; pp. 1-8.
Nanang, M. et al.: "Characteristics of TEMPO-oxidized cellulose fibril-based hydrogels induced by cationic ions and their properties", Cellulose, vol. 22, 2015; pp. 1993-2010.

(Continued)

*Primary Examiner* — Blessing M Fubara
(74) *Attorney, Agent, or Firm* — CANTOR COLBURN LLP

(57) ABSTRACT

The present application provides a method for preparing nanofibrillar cellulose product, the method comprising providing nanofibrillar cellulose, providing multivalent cations, contacting the nanofibrillar cellulose with the multivalent cations, and allowing reacting for a period of time to obtain cross-linked nanofibrillar cellulose product. The present application also provides a nanofibrillar cellulose product comprising nanofibrillar cellulose and multivalent cations, wherein the nanofibrillar cellulose is crosslinked by the multivalent cations.

25 Claims, 10 Drawing Sheets

(56) References Cited

OTHER PUBLICATIONS

Written Opinion for the corresponding International Application No. PCT/EP2019/062187; International Filing Date: May 13, 2019; Date of Mailing: Aug. 1, 2019; 7 pages.

Yao, J. et al.: "Macrofibers with High Mechanical Performance Based on Aligned Bacterial Cellulose Nanofibers", ACS Appl. Mater. Interfaces, vol. 9, 2017; pp. 20330-20339.

Nanang et al., "Characteristics of TEMPO-oxidized cellulose fibril-based hydrogels induced by cationic ions and their properties", Cellulose, vol. 22, 2015; pp. 1993-2010.

Hassan et al., "Membranes Based on Cellulose Nanofibers and Activated Carbon for Removal of *Escherichia coli* Bacteria from Water", Polymers, vol. 9, No. 335, 2017; 14 pages.

\* cited by examiner

NANOFIBRILLAR CELLULOSE PRODUCT AND A METHOD FOR MANUFACTURING THEREOF

CROSS-REFERENCE TO RELATED APPLICATIONS

This application is a National Stage application of PCT/EP2019/062187, filed May 13, 2019, which claims benefit of European Application No. 18397520.0 filed on Jun. 13, 2018, both of which are incorporated by reference herein in their entirety.

FIELD OF THE APPLICATION

The present application relates to crosslinked nanofibrillar cellulose products and methods for manufacturing thereof.

BACKGROUND

Cellulose may be fibrillated to obtain fibrillar cellulose, such as microfibrillar or nanofibrillar cellulose. Fibrillar cellulose refers to isolated cellulose fibrils or fibril bundles derived from cellulose raw material. Fibrillar cellulose, especially nanofibrillar cellulose, has a capability of forming viscous gel in water.

Nanofibrillar cellulose production techniques are based on mechanical fibrillation of aqueous dispersion of pulp fibers. The concentration of nanofibrillar cellulose in dispersions is typically very low, usually around 0.3-5%. After the fibrillation process, the obtained nanofibrillar cellulose material is a dilute viscoelastic hydrogel.

There is interest in making structural products from nanofibrillar cellulose by removing water to the extent that the product exists as a self-supporting structure in form of a membrane or other form.

However, the properties of the obtained membranes or other products needs improving. For example the membranes are brittle and lack elasticity and flexibility. Also user and environmentally friendly processes and biologically compatible and biodegradable products are desired.

SUMMARY

It was found out that multivalent cations can be used to control the formation of a nanofibrillar cellulose material, such as gels formed from nanofibrillar cellulose. The multivalent cations can be used to crosslink the nanofibrillar cellulose and therefore harden the gels. This limits their shrinkage during drying, such as lateral or longitudinal shrinkage of layers, coatings, sheets or membranes.

However, homogeneous mixing of soluble multivalent cations with the anionic gels may be challenging. Mixing of these components may lead to immediate, uncontrollable fibril aggregation and flock formation. It was also found out how certain structures, such as films, membranes, sheets or filaments, of anionic cellulose nanofibrils and multivalent cations can be prepared without the aggregation or flock formation. The main principle is to prepare the structure before the bridging with the multivalent cations.

The present application provides a method for preparing a nanofibrillar cellulose product, the method comprising
  providing anionically modified nanofibrillar cellulose,
  providing multivalent cations,
  contacting the anionically modified nanofibrillar cellulose with the multivalent cations, and
  allowing reacting for a period of time to obtain crosslinked nanofibrillar cellulose product.

The present application also provides a nanofibrillar cellulose product comprising nanofibrillar cellulose and multivalent cations, wherein the nanofibrillar cellulose is crosslinked by the multivalent cations. The product may be obtained with the method described herein. The nanofibrillar cellulose product may be formed into a variety of life science products, such as medical or scientific products described herein.

The present application also provides a layer comprising the nanofibrillar cellulose product. The layer may be for example a coating, a film, a sheet or a membrane.

The present application also provides a medical multilayer product comprising
  a layer comprising the nanofibrillar cellulose product, and
  a layer of gauze or nonwoven.

The present application also provides a medical product comprising the nanofibrillar cellulose product. The medical product may be a wound healing product.

The present application also provides a cell culture product comprising the nanofibrillar cellulose product.

The present application also provides use of the disclosed materials or crosslinked products for preparing the final products disclosed herein.

The main embodiments are characterized in the independent claims. Various embodiments are disclosed in the dependent claims. The embodiments recited in dependent claims and in the description are mutually freely combinable unless otherwise explicitly stated.

The obtained products exhibit enhanced mechanical strength and other properties, such as high tear strength (tear resistance), tensile strength, breaking strain, elasticity, flexibility and the like, especially at moist conditions. Compared to similar non-crosslinked products, which are brittle and poorly flexible when wetted, the obtained products tolerated handling and mechanical stress well without breaking. The shrinkage of the product, especially during dewatering, is low. The products may be used for example in medical and scientific products, such as dressing and patches, cell culture products, filters, and in food packings or coatings, and the like. The products are biodegradable and compatible with medical, scientific and food applications and uses, and can be used to replace non-biodegradable plastic films. The preparation process is safe and does not require highly reactive or harmful reagents or extreme conditions. It is possible to obtain products which may be dried and rewetted, and which still exhibit the desired properties after this treatment. When formed as films, the products were soft, smooth and elastic, and exhibited a skin-like feel, especially as air-dried. However, no softeners or the like additives were required to obtain such properties. The products can absorb and maintain high water content, which is advantageous in life science applications.

The products described herein are useful in medical applications, wherein the materials comprising nanofibrillar cellulose are in contact with living tissue. It was discovered that nanofibrillar cellulose provides unusual properties when it is applied for example onto skin. The products containing nanofibrillar cellulose as described herein are highly biocompatible with the living tissue and provide several advantageous effects. Without binding to any specific theory, it is believed that a layer comprising nanofibrillar cellulose provides a very high surface area, which, when applied against a skin or other tissue, absorbs water from the skin and forms special conditions between the tissue and the layer comprising nanofibrillar cellulose. The product may also be moistened to enhance the effect. Further, a thin gel layer will be formed onto the surface of the layer comprising nanofibrillar cellulose, and water molecules are present between this gel layer and the skin. The free hydroxyl groups in the nanofibrillar cellulose facilitate formation of hydrogen bonds between the material and water molecules. This will enhance contact with the skin and enable migration of fluids and/or agents from the skin to the product, or from the product to the skin.

When the products are used for covering wounds or other damages or injuries, for example as plasters, dressings, medical patches or parts of plasters, patches or dressings, several effects are provided. The usability of the products is good as the product may be applied and removed easily without being damaged, for example torn. When used for covering wounds the material of the product acts as an artificial skin, which protects the wound and will come loose when the wound heals. The flexibility and elasticity enable applying the product carefully on the target to stick to the contours of the target, so the products may be applied also to challenging targets. The product will not attach to a damaged skin in such irreversible way as conventional materials, which are usually very difficult to remove without damaging the healed area. The conditions between the product and the skin facilitate the healing of a damaged area.

Especially in products made of mostly or only from nanofibrillar cellulose the present crosslinked material provides flexibility, elasticity and mechanical strength unlike the brittle and non-flexible conventional nanofibrillar products, which are not suitable as wound healing or the like medial products.

The medical products of the embodiments are especially advantageous in the treatment of grafts, such as skin graft. The product may be used for covering the graft area and it acts as a protective layer. As the graft heals, the membrane forms a scab-like structure, which promotes the healing.

The products may be used for controllably and effectively delivering agents, such as therapeutic or cosmetic agents, to a patient or user.

The products may also exhibit remouldability. If the nanofibrillar cellulose contains moisture, it may also show good permeability. These properties are useful in medical and life science products, for example when the product is used as a dressing for healing wounds, or for delivering therapeutic or cosmetic agents, as a biological filter, or in cell culture use, wherein the product is used as cell culture medium.

Flexibility is a feature which is desired in many applications, such as in medical applications, and in films or filaments. The same applies to elasticity (elongation). For example, flexible and/or elastic cloths, patches and dressings comprising nanofibrillar cellulose are useful for applying onto skin, for example for covering wounds and other damages or injuries, such as burns, or for delivering active agents. The flexibility and elasticity of the fibrillar cellulose, for example as coating or as impregnated, may limit the flexibility and/or elasticity of the whole product, such as in the case of gauzes or nonwovens, so the enhanced flexibility and/or elasticity enables providing improved composite or layered products.

The medical products of the embodiments also provide high absorption capacity and absorption speed, which properties are desired in medical applications such as wound healing and the like. Large membranes may be prepared which may be used for covering large areas.

The products may be used in cell culture applications, for example as a support for cell culture. The nanofibrillar cellulose of the embodiments serves as a natural matrix, which resembles extracellular matrix, and provides structural scaffold for the cells and a network of interconnected pores for efficient cell migration, signaling and transfer of nutrition to the cells. Further, the product is biodegradable and non-toxic, and it can be degraded enzymatically without harming the cells, for example for harvesting the cells from the culture. The material does not contain any animal-based compounds, which could generate a risk of immunoreactions and different types of toxicity issues in cell culture and downstream applications.

DETAILED DESCRIPTION

Figure 1:
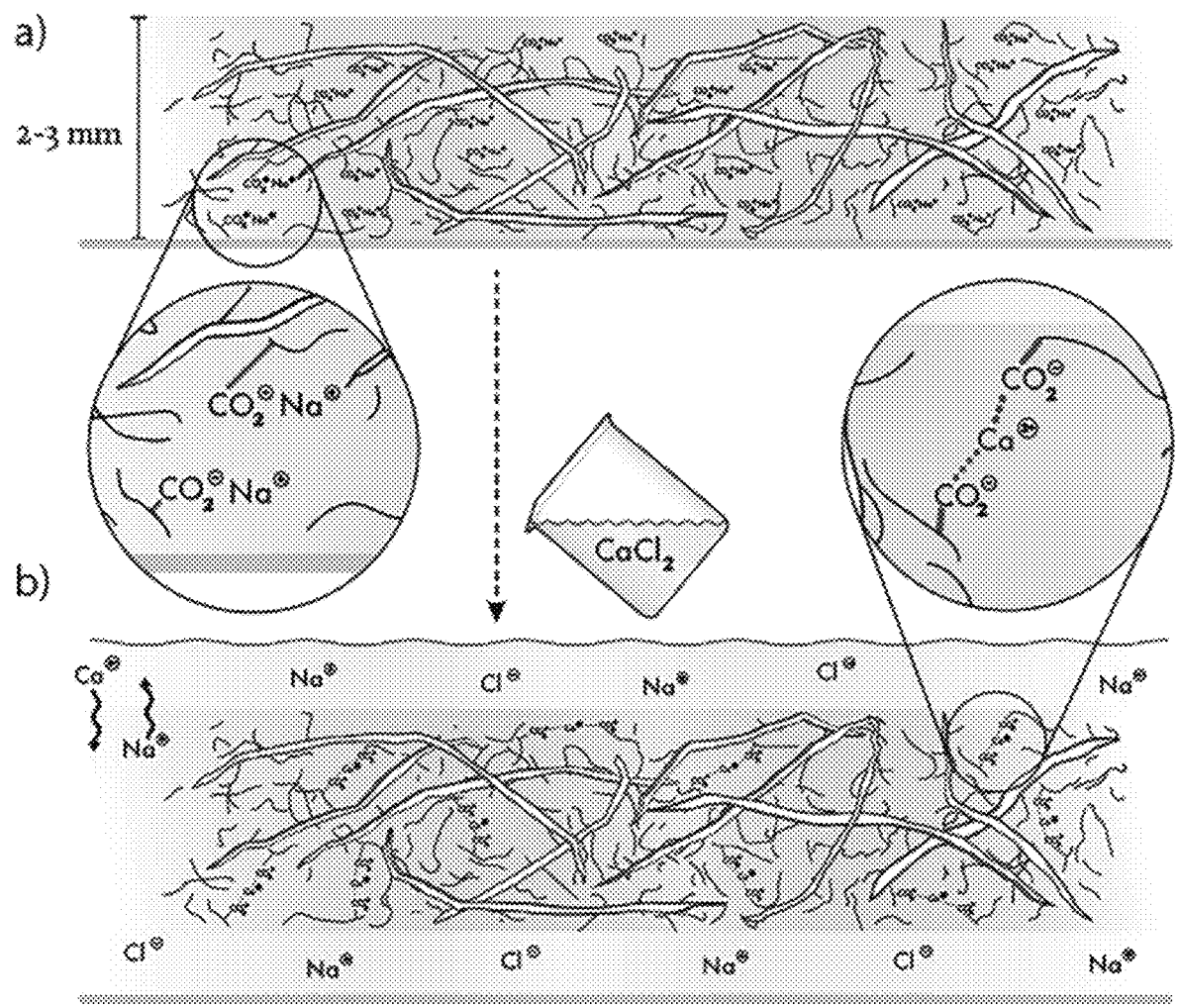
FIG. 1 shows the principle of preparing NFC/pulp films in $Ca^{2+}$ form. (a) The NFC/pulp mixture is spread on a support at 3% consistency. (b) The wet film on the support is immersed in aqueous $CaCl_2$) and kept there for 1-3 h to complete the ion exchange and solidification of the film before its drying.

In this specification, percentage values, unless specifically indicated otherwise, are based on weight (w/w). If any numerical ranges are provided, the ranges include also the upper and lower values. The concentrations are presented as dry weight, unless indicated otherwise. The percentages of the ingredients in the final products sum up to 100%. The final product may contain minor amounts of additives customary in the art.

In the methods for preparing the fibrillar cellulose products described herein, the method comprises
 providing anionically modified fibrillar cellulose,
 providing multivalent cations, more particularly one or more types of multivalent cations,
 contacting the fibrillar cellulose with the multivalent cations, and
 allowing reacting for a period of time to obtain cross-linked fibrillar cellulose product.

The nanofibrillar cellulose should be wet when it is contacted and/or reacted with the multivalent cations, for example it may be in hydrogel form. The nanofibrillar cellulose may have a water content for example at least 10% (w/w), at least 20% (w/w), or at least 50% (w/w), such as in the range of 20-99.9% (w/w), or 50-99.9% (w/w), such as 70-99.9% (w/w), or 80-99.9%, for example 90-99.5% (w/w). The nanofibrillar cellulose may be provided at said water content or it may be moisturized or wetted prior to contacting and/or reacting with the multivalent cations.

The fibrillar cellulose may be any type of cellulose which is fibrillated into such degree that the material exhibits properties typical for fibrillar cellulose, such as exposed free hydroxyl groups capable of forming bonds with the cellulose and water, and therefore also a capability of forming viscous gel in water. However anionically modified fibrillar cellulose is preferred. The anionically modified fibrillar cellulose may be for example anionically modified highly fibrillated or refined pulp, anionically modified microfibrillar cellulose or anionically modified nanofibrillar cellulose. Microfibrillar cellulose may be characterized with the average fibril diameter and/or length higher than the average fibril diameter and/or length of nanofibrillar cellulose, such as an average fibril diameter of less than 2 micrometers, such as 100-1000 nm, or 220-1000 nm, and/or a fibril length of 0.5-50 micrometers, such as 5-50 micrometers. Also the rheological properties are different.

The best results were however obtained by using highly fibrillated nanofibrillar cellulose, more particularly anionically modified nanofibrillar cellulose, especially oxidized nanofibrillar cellulose. In one embodiment the fibrillar cellulose is anionically modified nanofibrillar cellulose, such as described herein. It is possible to use nanofibrillar cellulose as the only fibrous material in the product. Fibrous material refers to material derived from fibers, including fibers and fibrils, which may be natural and synthetic.

One embodiment provides a method for preparing a nanofibrillar cellulose product, the method comprising
providing anionically modified nanofibrillar cellulose as the only fibrous material,
providing multivalent cations, such as multivalent metal cations,
contacting the anionic nanofibrillar cellulose with the multivalent cations, and
allowing reacting for a period of time to obtain crosslinked nanofibrillar cellulose product.

In a method called diffusion-aided bridging, also presented in FIG. 1, a homogeneous wet product or material, such as a film, a sheet, a membrane, a filter or a filament comprising anionically modified fibrillated cellulose fibers and/or fibrils, is prepared or provided first and then subjected to a treatment with an aqueous solution of the multivalent cations. The multivalent cations diffuse inside the structure and solidify it with time. The time required for the solidification depends on the thickness of the structure or material and the concentration of the multivalent cation in the system. After a suitable time and before drying, the structure can be subjected to a second treatment in water to remove excess of the multivalent cations. When dried, the structure will get unique properties.

Therefore, in one embodiment the multivalent cations are provided as an aqueous solution. The aqueous solution is applied to the fibrillar cellulose, which may be a product, such as an existing nanofibrillar cellulose product, i.e. the fibrillar cellulose material is contacted with an aqueous solution of the multivalent cations. The existing nanofibrillar cellulose product is a previously prepared product, such as a product having a form and/or shape, and which may be in solid or in gel form. It may have been dewatered or dried to a desired moisture or dry content.

The method may further comprise washing the fibrillar cellulose material after a period of time, i.e. after crosslinking, such as washing with aqueous solution. The period of time is a period required for the desired crosslinking to take place, and in may be minutes or hours, such as at least one minute, for example at least in the range of 1-240 minutes, or 30-240 minutes, such as 1-3 hours. The fibrillar cellulose material may be soaked in the aqueous solution of multivalent cations. It is also possible to add the aqueous solution to the fibrillar cellulose material and aid the penetration of the solution inside the product for example by using vacuum.

This may be carried out with vacuum-aided method and arrangement, which can be used for subsequent dewatering, for example by providing a filter onto which the fibrillar cellulose is applied, and providing vacuum through the filter to first apply the aqueous solution of multivalent cations into the product by using the vacuum, optionally shutting down the vacuum to allow the multivalent cations to react with the fibrillar cellulose, for example for 10 seconds to 3 hours, and thereafter dewatering the product by using the vacuum.

Figure 8:
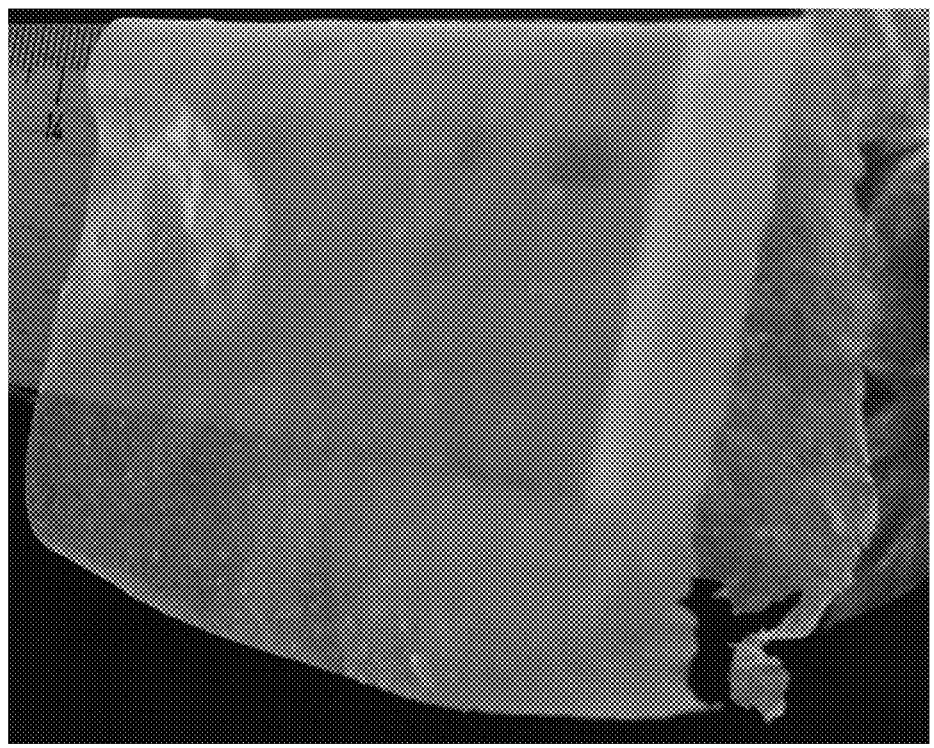
FIG. 8 shows a sample of a thin skin-like film of oxidized NFC and pulp; treated with aqueous $CaCl_2$).

In certain examples subsequent treatments of a wet film of anionic fibril cellulose and chemical pulp in aqueous calcium chloride and water resulted in, after drying the structure, to a wet skin-like structure that retained its humidity for a very long time at normal ambient conditions (FIG. 8). When a dried structure was immersed in water for some time, and then dried again, a paper-like rigid structure was obtained. When this structure was immersed in water repeatedly, its wet strength remained high.

Because the diffusion aided bridging might be challenging to realize industrially, an alternative way of making the bridges is provided. This is called time-triggered bridging. The main idea is to form a structure that contains the cellulosic fibers and/or fibrils, an insoluble (solid) multivalent cation salt and a chemical component or compound that releases acid with time. pH is lowered from neutral or slightly acidic to about 4, for example. The increasing acidity solubilizes the multivalent cation salt with time, after which the free cations can form the bridges.

In one embodiment the multivalent cations are provided as insoluble salt. In one embodiment the method further comprises providing an acid-releasing compound, wherein the released acid is capable of solubilizing the multivalent cations. More particularly, the acid-releasing compound is provided in an amount and/or form capable of providing acid to solubilize the multivalent cations, or at least a substantial amount of the multivalent cations, to obtain the desired crosslinking. The acid may be arranged to be released as delayed or prolonged release, i.e. over a period of time, which may be from seconds to hours, for example from 1 second to 24 hours, such as from 1 second to 1 hour. This results in delayed solubilization and release of the multivalent cations. Finally this results in delayed crosslinking of the fibrillar cellulose. This enables forming the final product before the material is fully crosslinked.

In one embodiment the multivalent cation is multivalent metal cation. It may comprise or may be selected from cations of calcium, magnesium, zinc, aluminum, gold, platinum and/or titanium. The specific multivalent cations may be used to provide further specific properties to the final products. For example gold may provide antimicrobial properties. Platinum and titanium may provide catalytic properties, such as photocatalytic properties in the case of titanium. Therefore it is possible to obtain materials exhibiting catalytic properties. Such materials may be used in photocatalytic applications, for example to provide reactive oxygen species in the material by illuminating the material with light. Such reactive oxygen species may be used to sterilize the material, such as filters, membranes, and other medical and life science products.

The insoluble salt may be a carbonate of the multivalent cation, such as calcium carbonate. The insoluble salt may be introduced as a powder or it may be provided as preprecipitated on cellulose fibers. In one example calcium carbonate is precipitated on cellulose fibers, which may be nanofibrillar cellulose fibrils and/or fibers of non-nanofibrillar cellulose.

Only small amounts of the additives multivalent cations and acid-releasing compounds are needed to accomplish almost complete bridging of the anionic fibers/fibrils, such as in the range of 0.1-3% (w/w), for example 0.1-2% (w/w). The delay time before the bridge formation can be controlled by the selection of the acid releasing component, concentrations of the agents, concentration of the fibrillar material, initial pH of the system, etc.

Due to the bridging, the fibril network consolidates less during drying and high strength is achieved at a lower material density in comparison with materials prepared without the bridging.

In one embodiment the contacting the nanofibrillar cellulose with the multivalent cations comprises forming a mixture of the nanofibrillar cellulose, the multivalent cations and the acid-releasing compound.

In one embodiment the acid-releasing compound is selected from an anhydride, more particularly acid anhydride, such as acetic anhydride (acetanhydride), and an ester, such as ethyl acetate.

The initial pH of the system, such as an aqueous suspension or gel containing the nanofibrillar cellulose and/or an aqueous solution containing the multivalent cation(s), may be in the range of 6-9, such as 7-8. When pH is lowered to solubilize the insoluble salt, it may be lowered to below 5, or below 4.5, such as to 4.5-3, or to 3.5-4.5.

Tear strength of a layer or other structure may be further enhanced by adding an amount of non-fibrillar fibers in a membrane or a structure comprising the fibrillar cellulose, such as synthetic or natural fibers, for example cellulose. The non-fibrillar fibers may be called also as coarse fibers and/or long fibers, which may be natural fibers, for example wood fibers, which may be softwood or hardwood, such as pulp, or from non-wood material. Even a relative small amount of non-fibrillar fibers, such as cellulose fibers, may effectively enhance the tear strength. In the preparation process of a membrane the enhanced tear strength also facilitates the removal of the dried membrane from a support, such as from a filter fabric, as the membrane is not prone to tearing. Non-fibrillar cellulose or other fibers may also provide porosity to the final product, which may be desired for example in medical applications, in filters, and the like. The non-fibrillar fibers may be also used for carrying the insoluble multivalent cations, such as calcium carbonate. An amount of non-fibrillar cellulose or other fibers may also enhance dewatering. The non-fibrillar fibers may be also called as non-nanofibrillar fibers, especially when the fibrillar cellulose is nanofibrillar cellulose. Such a product containing non-fibrillar fibers may be for example a nonwoven, a paper or a board.

Examples of suitable non-fibrillar natural fibers include, pulp, such as mechanical pulp, chemical pulp, chemithermomechanical pulp, steam explosion pulp, bacterial cellulose, kraft pulp, and flax fibers. Other non-wood fibers may be used as well. The length of the non-fibrillar natural fibers may be 10 or 50 micrometers or more, or 100 or 500 micrometers or more, such as in the range of 0.5-100 mm, or in the range of 1-100 mm. The non-fibrillar fibers may be long fibers having a length of 5 mm or more, such as in the range of 5-100 mm, or 5-50 mm.

In one example the method comprises providing and mixing non-fibrillar fibers, such as synthetic or natural fibers, which may be wood or non-wood fibers, with the fibrillar cellulose before contacting with the multivalent cations. This may be in an amount in the range of 0.1-99.9% (w/w), or 0.1-95% (w/w), such as in the range of 0.1-70% (w/w), of total fibrous material. The natural fibers may be pulp, such as chemical pulp or kraft pulp. Such pulp is in general conventional or regular pulp or cellulose and it may be also called as macrofibrillar pulp or macrofibrillar cellulose. In one example the non-fibrillar pulp is unrefined or moderately refined pulp, which may be characterized for example by pulp freeness, which may be 50° SR or less, or 40° SR or less. It is also possible to use more refined pulp, such as pulp having an SR value in the range of 50-70° or 50-90°. The .SR value (Schopper-Riegler value) may be used to determine the refining degree of cellulose. It can be determined by ISO5267. The Schopper-Riegler test is designed to provide a measure of the rate at which a dilute suspension of pulp may be dewatered. It has been shown that the drainability is related to the surface conditions and swelling of the fibres, and constitutes a useful index of the amount of mechanical treatment to which the pulp has been subjected.

Said two main starting materials may also be called as fractions, such as a fibrillar cellulose fraction and a non-fibrillar fiber fraction. The fibrillar cellulose fraction may be the main fraction of the fibrous material, such as cellulosic material, of the product, or the dispersion for preparing the product, for example comprising 20-99.9% (w/w) of fibrillar cellulose of the dry weight of total fibrous material, such as 20-70% (w/w). However it is also possible to use a larger fraction of non-fibrillar fibers. The ratio of fibrillar cellulose to non-fibrillar fibers may be in the range of 10:90 to 90:10, or 20:80 to 80:20, such as 30:70 to 70:30. In one specific example the ratio of fibrillar cellulose to non-fibrillar fibers is 20:80 to 40:60, such as about 30:70.

The product, or the dispersion for preparing the product, may contain nanofibrillar cellulose in the range of 0.1-100% (w/w) of the dry weight of the product or the dispersion.

Due to the crosslinking, it is also possible to use a smaller fraction of fibrillar cellulose, which is expensive material. In examples the product comprises, for example when the fibrillar cellulose is as a coating on a fibrous product, or the dispersion for preparing the product comprises 0.1-70% (w/w) of fibrillar cellulose of the dry weight of the dispersion or the product, such as 0.2-50% (w/w), 0.2-30% (w/w), 0.2-20% (w/w), 0.2-15% (w/w), 0.2-10% (w/w), 1-20% (w/w), 1-10% (w/w) or 5-10% (w/w). For example it is possible to us fibrillar cellulose as a coating in the range of 3-12 g, such as 5-10 g per square meter for a paper, which may have a grammage in the range of 80-120 g/m$^2$, for example 100 g/m$^2$.

The non-fibrillar fiber may be also a minor fraction or portion of the fiber and fibril material, such as cellulosic material, of the product. In one embodiment the fibrillar cellulose product comprises an amount of non-fibrillar fiber, such as pulp, in the range of 0.1-70% (w/w) of total fibrous material, for example in the range of 0.1-60% (w/w), 0.1-50% (w/w), 0.1-40% (w/w), 0.1-30% (w/w), 0.1-20% (w/w), 0.1-10% (w/w), 0.5-10% (w/w), 1-10% (w/w), 0.5-5% (w/w), 1-5% (w/w), 0.5-3% (w/w) or 1-3% (w/w) of dry weight of the total material or product. "Total material" as used herein refers to the dry weight of all the fibers, fibrils, multivalent cations and other possible ingredients present in the product.

However, in one embodiment the product does not contain any non-fibrillar fibers, i.e. the amount of non-fibrillar fibers is 0%. Therefore the fibrillar cellulose is the only fibrous or fibrillar material in the final product.

Also other auxiliary agents or additives may be added to the mixture, for example in an amount in the range of 0.01-2% (w/w). For example salts, such as salts of monovalent metals, for example NaCl, may be added. The added salt may enhance the flexibility of the obtained products, for example by binding water to the structure.

In one embodiment the method comprises forming the fibrillar cellulose into a layer, such as a coating, a film, a sheet or a membrane; a filter; a filament or fibrillar cellulose bodies or hydrogel bodies. The fibrillar cellulose may be formed into such forms or products before or after crosslinking. Also other structures or forms may be formed, for example by using a mould. One example of the obtained structure is a hollow fiber. Preferably the fibrillar cellulose is formed into said forms or products before the crosslinking has begun or is completed, such as before the crosslinked product is obtained. The completed crosslinking will fix the final form of the product. One example of the obtained structure is cell culture material or composition, which may contain dried or hydrogel material, such as nanofibrillar cellulose bodies, hydrogel bodies or other similar separate entities.

In one embodiment the method comprises providing one or more therapeutic agent(s) and/or one or more cosmetic agent(s) and mixing the agent(s) with the nanofibrillar cellulose, before or after contacting with the multivalent cations. In this way the therapeutic and/or cosmetic agent(s) will be included in the final product and may be released from the product when applied for example onto skin. The final product may also be impregnated with the agent(s).

When one or more of the multivalent cations and any auxiliary agent(s) discussed herein are added to the nanofibrillar cellulose, a mixture of these ingredients is obtained, which may be an aqueous suspension. The method may further comprise foaming the fibrillar cellulose, or the product, such as foaming the obtained mixture. A foaming agent may be used to obtain a foam. The method may therefore comprise adding one or more foaming agent to the mixture and foaming the mixture. The multivalent cation(s) may be added to the mixture before foaming, or the multivalent cation(s) may be added to the foamed mixture.

Therapeutic or cosmetic agent(s) may be added to the mixture before foaming, or one or more such agent(s) may be added to the foamed mixture.

The foam may be formed into a layer, such as a sheet. This may be carried out by using multi-layer techniques, so a multi-layer product is obtained. In general, the product may contain one or more layer(s) such as two or more layers. The different layers may contain different properties, for example they may have different compositions, thicknesses, densities etc. and/or they may contain different therapeutic or cosmetic agent(s). In one example a product is formed wherein a first layer, which is to be applied against skin, contains nanofibrillar cellulose and optionally one or more active agent(s), such as therapeutic, cosmetic and/or antimicrobial agents, which layer also maintains desired moisture content, and a second layer would contain at least non-nanofibrillar fibers, such as long fibers, for example long softwood fibers, to provide reinforcing properties. Also a third layer may be formed, which may act as the outer layer, which could have antimicrobial and/or dirt repellent properties.

Foamed product can be dewatered more easily than a water-fiber suspension, and the pore size of the material is easier to control. The foam may be also modified chemically and/or enzymatically to provide for example antiseptic properties. Foamed products may be used as bandages or other medical products as described herein, for example to cover wounds and other damages.

The method may further comprise dewatering the crosslinked nanofibrillar cellulose product. Dewatering refers to a water removal from material, usually to a desired dry or moisture content. Dewatering may be drying. The drying may be air drying, vacuum drying or freeze drying (lyophilization). The material may be dried into a suitable form, such as into a layer, for example a coating, a film, a sheet, a membrane, a filter, or a filament, nanofibrillar cellulose or hydrogel bodies, such as separate spherical entities or the like. The final product may be a medical product, such as patch or a dressing comprising the film, a sheet, a filament, a filter, cell culture material or other form suitable for the desired use. The final crosslinked nanofibrillar cellulose product may be completely or partially dewatered or dried, or it may be left undried, and the water content of the final product may be adjusted for the desired purpose or use of the product. The final product may be therefore present as a gel or a dried or dewatered product, layered or non-layered, as described herein.

The methods may be used for preparing any of the products disclosed herein. The products may be life science products, which include materials and products which are used in contact with living bio biological matter, such as skin, tissue, cells, biochemical compounds and the like. The products may be used in a variety of applications in the field of medicine, diagnostics and research, but also in cosmetic applications. The medical products discussed herein may be also used in the other life science applications.

One embodiment provides a nanofibrillar cellulose product comprising nanofibrillar cellulose, preferably anionic nanofibrillar cellulose, and multivalent cations, wherein the nanofibrillar cellulose is crosslinked by the multivalent cations. The amount of the multivalent cations in the final products may be in the range of 30-500 mmol/kg, such as 30-300 mmol/kg, for example in the range of 150-250 mmol/kg for calcium and in the range of 40-70 mmol/kg for magnesium. This may depend on the other treatments, such as washing. For example after 15 min first water treatment the content of calcium and magnesium may be in the range of 0.15-0.25 mmol/g, such as 0.16-0.23 mmol/g. On the contrary, the second immersion inside of water, such as about 1 h, may remove most of magnesium from the films, so the calcium and magnesium content may be in the range of 0.05-0.06 mmol/g. The crosslinking can be explained in term of the partial bond formation between one divalent cation and either two or three carboxylate groups (e.g. MFC—COO-M-COO-MFC and/or MFC—COO-MCl, wherein M is a metal ion). It is possible to detect the divalent cations, such as calcium and magnesium, in the dried films.

The concentration of the multivalent cation may be detected from the final product, for example by analyzing ash, i.e. inorganic content after ignition of the product. The multivalent cations may be detected and determined by using routine methods, for example instrumentally. The multivalent cation content combined with one or more other properties measured from the final product, such as elongation, density, tensile index and/or tear strength and the like, may be used to efficiently characterize the final products.

The crosslinking obtained in the present method by the multivalent cations is ionic crosslinking, i.e. non-covalent crosslinking, so that the cellulosic polymer chains are linked to each other by ionic bonds. Such crosslinking may also be classified as physical crosslinking, which is different from chemical crosslinking. When polymer chains are crosslinked, the material is rigidified. When ionic crosslinking is obtained, the material may be reformable, i.e. the crosslinking may be reversible or breakable, which is not the case with covalent crosslinking, which is irreversible. Ionic crosslinking does not require highly reactive reagents, so the preparation method is safe and non-toxic. The crosslinking may be carried out when water is present, which has an effect to the obtained product. For example the structure does not collapse when it contains water, as would be the case with non-crosslinked materials. It is therefore possible to obtain more flexible products and products having a different density.

Further, it is not only the ionic bonds which contribute the formation of the final rigidified product. When the product containing the multivalent cations is dewatered, such as dried, also bonds between cellulosic chains are formed which do not include the multivalent cations. These bonds may be permanent and they support the structure of the product. These bonds are created even in only part of the water is removed. Also hydrogen bond are formed. After said structure has been formed, the product may be rewetted and dewatered again without loosing the obtained properties. Therefore the ionic bonding is important especially when forming the structure, i.e. at the beginning of the preparation, but the final product may contain also covalent bonds between the cellulosic chains. The crosslinking in the final product may not be homogenous but the product may contain a gradient in respect of the formed crosslinks, which is caused by the diffusion of multivalent cations into the material, effect of diffused water of other aqueous solution to the pH, concentration, ion content or the like in the fibrillar cellulose, and the like effect during the formation of the material. For example the surface of the product may contain more crosslinks and/or multivalent cations compared to the inner part of the product The final product may be examined by using electron microscopy, for example SEM, to detect the crosslinking obtained in the method. It is also possible to determine equilibrium water content of the final product, which is a measure of how well the product absorbs water. The water content may be determined at certain humidity and at zero humidity, and the weights of the product samples may be measured. As described herein, the inventive product absorbs more water than a prior art product made with another method.

One embodiment provides a nanofibrillar cellulose product, such as the product described in previous, obtained with any of the methods disclosed herein.

In one embodiment the product is in a form of, or is incorporated in, a layer, which may be a coating, or a film, a sheet, or a membrane, which terms may be used interchangeably, or in a form of a filter, a paper, a nonwoven, or a filament. Such films are flexible and durable and they exhibit also barrier properties, such as water or grease barrier properties. Films may be used instead of conventional plastic films, for example in packages, as wrapping, as coating, in labels, and the like.

In one embodiment the nanofibrillar cellulose product is foamed. In one embodiment the product comprises at least one foamed layer, as disclosed in previous.

In one embodiment the nanofibrillar cellulose product is in a form of a filament, which may also be a fibre, such as a stable fibre. A filament refers to an elongate structure, such as a thread-like structure. A filament may have an average diameter in the range of 1-50 µm, such as about 10 µm. The length of the filament may be over 100 µm, such as over 500 µm, for example in the range of 0.1-10000 mm. A filament may be a part of a fiber, such as a hollow fiber or a non-hollow fiber, or a yarn, which may comprise only such filaments as main material, or also other types of materials, such as filaments derived from other natural fibers, such as cellulose derivatives, and/or synthetic filaments. The filaments comprising the present crosslinked fibrillar cellulose may act as reinforcing material in such composite materials. Filaments may be prepared by spinning fibrillar cellulose, especially cellulose nanofibrils by dry, wet or dry-jet wet spinning methods, which are solvent spinning techniques. Wet and dry spinning are techniques which may be applied on NFC spinning from hydrogels without added polymers. TEMPO oxidation as a pretreatment has a positive effect to the spinning process, which may be caused by the increased degree of polymerization (DP) in the fibrillar cellulose. Cellulose solution with a high DP can be drawn more easily than that from a low-DP solution and thus spun into a stronger and stiffer regenerated filament. Also carboxymethylation has a positive effect to the spinning.

Filaments may be used in textiles, fabrics or cloths, such as woven or nonwoven materials. By one definition a woven is a thin, translucent fabric with a loose open weave. In technical terms a woven is a weave structure in which the weft yarns are arranged in pairs and are crossed before and after each warp yarn keeping the weft firmly in place. A nonwoven comprises fibers pressed together to resemble a weave, which provides for example improved wicking and greater absorbent capacity. Therefore the product may be also a textile, a fabric, a cloth or the like. Filaments may be also used in life science products.

In one embodiment the nanofibrillar cellulose product is a filter, or a filter is provided comprising the nanofibrillar cellulose product. A filter may be used in medical or scientific application, or in other applications, such as for filtrating water or other aqueous liquids, for recovering particles from an aqueous suspension, or as an osmotic filter or membrane, or for dewatering material.

In one example the nanofibrillar cellulose product is in a form of a paper, a cardboard or a nonwoven, or a paper, a cardboard or a nonwoven is provided comprising the product. The paper, cardboard or the nonwoven may be a specialty paper. such as fine papers and special products, for example a coated or an impregnated paper, such as tissue papers, printing papers, labels, release liners, or papers or cardboards having barrier properties. In general the paper, the cardboard or the nonwoven product may be a wet-laid product, which may be prepared using any suitable wet-laying method. A coated paper or cardboard may comprise a layer or a coating of the crosslinked fibrillar cellulose product, for example on a cellulosic fibrous layer, which may represent a conventional paper web. A nonwoven may be impregnated or coated with the crosslinked fibrillar cellulose. Examples of nonwovens include napkins, wipes, filters, cloths, textiles, and the like. A paper or a cardboard and a nonwoven may differ in the average fiber length, which is higher in the nonwoven, such as 5 mm or higher, and in density, grammage, thickness and the like properties.

The crosslinked fibrillar cellulose may provide properties, such as grease barrier properties, to the papers, cardboards, nonwovens or other products discussed herein.

In one example the product is a packing, such as a food packing, or a part of a packing. The packing may comprise the paper, cardboard, nonwoven or fibrillar cellulose films discussed herein. The packing may exhibit barrier properties, such as grease barrier properties.

In one example the product is a coating, such as a coating on a food product, a pharmaceutical product, on a paper, on a cardboard, on a filter, on a nonwoven, or the like. The food or food product may be human food, or it may be animal feed or fodder.

In one embodiment the nanofibrillar cellulose product is a medical product.

In one embodiment the product comprises one or more therapeutic agent. In one embodiment the product comprises one or more cosmetic agent.

In one embodiment the nanofibrillar cellulose product is cell culture or cell delivery material, such as cell culture or cell delivery composition. Cell culture material may be continuous or discontinuous material, such as a continuous dried or dewatered material or gel, such as a sheet or a plurality of separate or interconnected entities. For example the product may be a three-dimensional discontinuous entity for culturing of cells comprising an aqueous medium; and dried, dewatered or hydrogel bodies comprising the cellulose nanofibrils material suspended in the aqueous medium.

Nanofibrillar Cellulose

The starting material for the preparation process is usually nanofibrillar cellulose obtained from the disintegration of fibrous raw material and existing at a relatively low concentration homogeneously distributed in water due to the disintegration conditions. The starting material may be an aqueous gel at a concentration of 0.2-10% (w/w), for example 0.2-5% (w/w). The nanofibrillar cellulose may be obtained directly from the disintegration of fibrous raw material.

The nanofibrillar cellulose is prepared generally from cellulose raw material of plant origin, such as wood or non-wood origin. The raw material may be based on any plant material that contains cellulose. The raw material may also be derived from certain bacterial fermentation processes. The nanofibrillar cellulose is preferably made of plant material. In one example the fibrils are obtained from non-parenchymal plant material. In such case the fibrils may be obtained from secondary cell walls. One abundant source of such cellulose fibrils is wood fibres. The nanofibrillar cellulose is manufactured by homogenizing wood-derived fibrous raw material, which may be chemical pulp. Cellulose fibers are disintegrated to produce fibrils which have an average diameter of only some nanometers, which may be 200 nm at the most, and gives a dispersion of fibrils in water. The fibrils originating from secondary cell walls are essentially crystalline with degree of crystallinity of at least 55%. Such fibrils may have different properties than fibrils originated from primary cell walls, for example the dewatering of fibrils originating from secondary cell walls may be more challenging. In general in the cellulose sources from primary cell walls, such as sugar beet, potato tuber and banana rachis, the microfibrils are easier to liberate from the fibre matrix than fibrils from wood, and the disintegration requires less energy. However, these materials are still somewhat heterogeneous and consist of large fibril bundles.

Non-wood material may be from agricultural residues, grasses or other plant substances such as straw, leaves, bark, seeds, hulls, flowers, vegetables or fruits from cotton, corn, wheat, oat, rye, barley, rice, flax, hemp, manila hemp, sisal hemp, jute, ramie, kenaf, bagasse, bamboo or reed. The cellulose raw material could be also derived from the cellulose-producing micro-organism. The micro-organisms can be of the genus *Acetobacter, Agrobacterium, Rhizobium, Pseudomonasor Alcaligenes*, preferably of the genus *Acetobacter* and more preferably of the species *Acetobacter xylinum* or *Acetobacter pasteurianus*.

It was found out that nanofibrillar cellulose obtained from wood cellulose is preferable for medical products described herein. Wood cellulose is available in large amounts, and the preparation methods developed for wood cellulose enable producing nanofibrillar materials suitable for medical products. Nanofibrillar cellulose obtained from wood also exhibit properties which are preferred in medical products. Wood may be from softwood tree such as spruce, pine, fir, larch, douglas-fir or hemlock, or from hardwood tree such as birch, aspen, poplar, alder, *eucalyptus*, oak, beech or acacia, or from a mixture of softwoods and hardwoods.

In one embodiment the nanofibrillar cellulose is obtained from wood pulp. In one embodiment the nanofibrillar cellulose is obtained from hardwood pulp. In one example the hardwood is birch. In one embodiment the nanofibrillar cellulose is obtained from softwood pulp. In one embodiment the wood pulp is chemical pulp. Chemical pulp may be desired for medical or scientific products. Chemical pulp is pure material and may be used in a wide variety of applications. For example chemical pulp lack the pitch and resin acids present in mechanical pulp, and it is more sterile or easily sterilisable. Further, chemical pulp is more flexible and provides advantageous properties for example in medical patches or dressings and other materials applied on living tissue.

As used herein, the term "nanofibrillar cellulose" refers to cellulose fibrils or fibril bundles separated from cellulose-based fiber raw material. These fibrils are characterized by a high aspect ratio (length/diameter). The average length of nanofibrillar cellulose (the median length of particles such as fibrils or fibril bundles) may exceed 1 μm, and in most cases it is 50 μm or less. If the elementary fibrils are not completely separated from each other, the entangled fibrils may have an average total length for example in the range of 1-100 μm, 1-50 μm, or 1-20 μm. However, if the nanofibrillar material is highly fibrillated, the elementary fibrils may be completely or almost completely separated and the average fibril length is shorter, such as in the range of 1-10 μm or 1-5 μm. This applies especially for native grades of fibrils which are not shortened or digested, for example chemically, enzymatically or mechanically. However, strongly derivatized nanofibrillar cellulose may have a shorter average fibril length, such as in the range of 0.3-50 μm, such as 0.3-20 μm, for example 0.5-10 μm or 1-10 μm. Especially shortened fibrils, such as enzymatically or chemically digested fibrils, or mechanically treated material, may have an average fibril length of less than 1 μm, such as 0.1-1 μm, 0.2-0.8 μm or 0.4-0.6 μm. The fibril length and/or diameter may be estimated microscopically, for example using CRYO-TEM, SEM or AFM images.

The average diameter (width) of nanofibrillar cellulose is less than 1 μm, or 500 nm or less, such as in the range of 1-500 nm, typically 200 nm or less, such as in the range of 1-200 nm, 2-200 nm, 2-100 nm, or 2-50 nm, even 2-20 for highly fibrillated material. The smallest fibrils are in the scale of elementary fibrils, the average diameter being typically in the range of 2-12 nm. The dimensions and size distribution of the fibrils depend on the refining method and efficiency. In case of native nanofibrillar cellulose, the average diameter of a fibril may be in the range of 5-100 nm, for example in the range of 10-50 nm. Nanofibrillar cellulose is characterized by a large specific surface area and a strong ability to form hydrogen bonds. In water dispersion, the nanofibrillar cellulose typically appears as either light or turbid gel-like material. Depending on the fiber raw material, nanofibrillar cellulose obtained from plants, especially wood, may also contain small amounts of other plant components, especially wood components, such as hemicellulose or lignin. The amount is dependent on the plant source. Often used parallel names for nanofibrillar cellulose include nanofibrillated cellulose (NFC) and nanocellulose.

In general cellulose nanomaterials may be divided into categories according to TAPPI W13021, which provides standard terms for cellulose nanomaterials. Not all of these materials are nanofibrillar cellulose. Two main categories are "Nano objects" and "Nano structured materials". Nano-structured materials include "Cellulose microcrystals" (sometimes called as CMC) having a diameter of 10-12 μm and length:diameter ratio (L/D)<2, and "Cellulose microfibrils" having a diameter of 10-100 nm and a length of 0.5-50 μm. Nano objects include "Cellulose nanofibers", which can be divided into "Cellulose nanocrystals" (CNC) having a diameter of 3-10 nm and L/D>5, and "Cellulose nanofibrils" (CNF or NFC), having a diameter of 5-30 nm and L/D>50.

Different grades of nanofibrillar cellulose may be categorized based on three main properties: (i) size distribution, length and diameter (ii) chemical composition, and (iii) rheological properties. To fully describe a grade, the properties may be used in parallel. Examples of different grades include native (or non-modified) NFC, oxidized NFC (high viscosity), oxidized NFC (low viscosity), carboxymethylated NFC and cationized NFC. Within these main grades, also sub-grades exist, for example: extremely well fibrillated vs. moderately fibrillated, high degree of substitution vs. low degree of substitution, low viscosity vs. high viscosity etc. The fibrillation technique and the chemical pre-modification have an influence on the fibril size distribution. Typically, non-ionic grades have wider average fibril diameter (for example in the range of 10-100 nm, or 10-50 nm) while the chemically modified grades are a lot thinner (for example in the range of 2-20 nm). Distribution is also narrower for the modified grades. Certain modifications, especially TEMPO-oxidation, yield shorter fibrils.

Depending on the raw material source, e.g. hardwood vs. softwood pulp, different polysaccharide composition exists in the final nanofibrillar cellulose product. Commonly, the non-ionic grades are prepared from bleached birch pulp, which yields high xylene content (25% by weight). Modified grades are prepared either from hardwood or softwood pulps. In those modified grades, the hemicelluloses are also modified together with the cellulose domain. Most probably, the modification is not homogeneous, i.e. some parts are more modified than others. Thus, detailed chemical analysis is usually not possible as the modified products are complicated mixtures of different polysaccharide structures.

In an aqueous environment, a dispersion of cellulose nanofibers forms a viscoelastic hydrogel network. The gel is formed already at relatively low concentrations of for example 0.05-0.2% (w/w) by dispersed and hydrated entangled fibrils. The viscoelasticity of the NFC hydrogel may be characterized for example with dynamic oscillatory rheological measurements.

The nanofibrillar cellulose hydrogels exhibit characteristic rheological properties. For example they are shear-thinning or pseudoplastic materials, which means that their viscosity depends on the speed (or force) by which the material is deformed. When measuring the viscosity in a rotational rheometer, the shear-thinning behavior is seen as a decrease in viscosity with increasing shear rate. The hydrogels show plastic behavior, which means that a certain shear stress (force) is required before the material starts to flow readily. This critical shear stress is often called the yield stress. The yield stress can be determined from a steady state flow curve measured with a stress controlled rheometer. When the viscosity is plotted as function of applied shear stress, a dramatic decrease in viscosity is seen after exceeding the critical shear stress. The zero shear viscosity and the yield stress are the most important rheological parameters to describe the suspending power of the materials. These two parameters separate the different grades quite clearly and thus enable classification of the grades.

The dimensions of the fibrils or fibril bundles are dependent for example on the raw material, the disintegration method and number of disintegration runs. Mechanical disintegration of the cellulose raw material may be carried out with any suitable equipment such as a refiner, grinder, disperser, homogenizer, colloider, friction grinder, pin mill, rotor-rotor dispergator, ultrasound sonicator, fluidizer such as microfluidizer, macrofluidizer or fluidizer-type homogenizer. The disintegration treatment is performed at conditions wherein water is sufficiently present to prevent the formation of bonds between the fibers.

In one example the disintegration is carried out by using a disperser having at least one rotor, blade or similar moving mechanical member, such as a rotor-rotor dispergator, which has at least two rotors. In a disperser the fiber material in dispersion is repeatedly impacted by blades or ribs of rotors striking it from opposite directions when the blades rotate at the rotating speed and at the peripheral speed determined by the radius (distance to the rotation axis) in opposite directions. Because the fiber material is transferred outwards in the radial direction, it crashes onto the wide surfaces of the blades, i.e. ribs, coming one after the other at a high peripheral speed from opposite directions; in other words, it receives a plurality of successive impacts from opposite directions. Also, at the edges of the wide surfaces of the blades, i.e. ribs, which edges form a blade gap with the opposite edge of the next rotor blade, shear forces occur, which contribute to the disintegration of the fibers and detachment of fibrils. The impact frequency is determined by the rotation speed of the rotors, the number of the rotors, the number of blades in each rotor, and the flow rate of the dispersion through the device.

In a rotor-rotor dispergator the fiber material is introduced through counter-rotating rotors, outwards in the radial direction with respect to the axis of rotation of the rotors in such a way that the material is repeatedly subjected to shear and impact forces by the effect of the different counter-rotating rotors, whereby it is simultaneously fibrillated. One example of a rotor-rotor dispergator is an Atrex device.

Another example of a device suitable for disintegrating is a pin mill, such as a multi-peripheral pin mill. One example of such device, as described in U.S. Pat. No. 6,202,946 B1, includes a housing and in it a first rotor equipped with collision surfaces; a second rotor concentric with the first rotor and equipped with collision surfaces, the second rotor being arranged to rotate in a direction opposite to the first rotor; or a stator concentric with the first rotor and equipped with collision surfaces. The device includes a feed orifice in the housing and opening to the center of the rotors or the rotor and stator, and a discharge orifice on the housing wall and opening to the periphery of the outermost rotor or stator.

In one example the disintegrating is carried out by using a homogenizer. In a homogenizer the fiber material is subjected to homogenization by an effect of pressure. The homogenization of the fiber material dispersion to nanofibrillar cellulose is caused by forced through-flow of the dispersion, which disintegrates the material to fibrils. The fiber material dispersion is passed at a given pressure through a narrow through-flow gap where an increase in the linear velocity of the dispersion causes shearing and impact forces on the dispersion, resulting in the removal of fibrils from the fiber material. The fiber fragments are disintegrated into fibrils in the fibrillating step.

As used herein, the term "fibrillation" generally refers to disintegrating fiber material mechanically by work applied to the particles, where cellulose fibrils are detached from the fibers or fiber fragments. The work may be based on various effects, like grinding, crushing or shearing, or a combination of these, or another corresponding action that reduces the particle size. The energy taken by the refining work is normally expressed in terms of energy per processed raw material quantity, in units of e.g. kWh/kg, MWh/ton, or units proportional to these. The expressions "disintegration" or "disintegration treatment" may be used inter-changeably with "fibrillation".

The fiber material dispersion that is subjected to fibrillation is a mixture of fiber material and water, also herein called "pulp". The fiber material dispersion may refer generally to whole fibers, parts (fragments) separated from them, fibril bundles, or fibrils mixed with water, and typically the aqueous fiber material dispersion is a mixture of such elements, in which the ratios between the components are dependent on the degree of processing or on the treatment stage, for example number of runs or "passes" through the treatment of the same batch of fiber material.

One way to characterize the nanofibrillar cellulose is to use the viscosity of an aqueous solution containing said nanofibrillar cellulose. The viscosity may be for example Brookfield viscosity or zero shear viscosity. The specific viscosity, as described herein, distinguishes nanofibrillar cellulose from non-nanofibrillar cellulose.

In one example the apparent viscosity of the nanofibrillar cellulose is measured with a Brookfield viscometer (Brookfield viscosity) or another corresponding apparatus. Suitably a vane spindle (number 73) is used. There are several commercial Brookfield viscometers available for measuring apparent viscosity, which all are based on the same principle. Suitably RVDV spring (Brookfield RVDV-III) is used in the apparatus. A sample of the nanofibrillar cellulose is diluted to a concentration of 0.8% by weight in water and mixed for 10 min. The diluted sample mass is added to a 250 ml beaker and the temperature is adjusted to 20° C.±1° C., heated if necessary and mixed. A low rotational speed 10 rpm is used.

The nanofibrillar cellulose provided as a starting material in the method may be characterized by the viscosity it provides in a water solution. The viscosity describes, for example, the fibrillation degree of the nanofibrillar cellulose. In one embodiment the nanofibrillar cellulose when dispersed in water provides a Brookfield viscosity of at least 2000 mPa·s, such as at least 3000 mPa·s, measured at a consistency of 0.8% (w/w) and at 10 rpm. In one embodiment the nanofibrillar cellulose, when dispersed in water, provides a Brookfield viscosity of at least 10000 mPa·s measured at a consistency of 0.8% (w/w) and at 10 rpm. In one embodiment the nanofibrillar cellulose, when dispersed in water, provides a Brookfield viscosity of at least 15000 mPa·s measured at a consistency of 0.8% (w/w) and at 10 rpm. Examples of Brookfield viscosity ranges of said nanofibrillar cellulose when dispersed in water include 2000-20000 mPa·s, 3000-20000 mPa·s, 10000-20000 mPa·s, 15000-20000 mPa·s, 2000-25000 mPa·s, 3000-25000 mPa·s, 10000-25000 mPa·s, 15000-25000 mPa·s, 2000-30000 mPa·s, 3000-30000 mPa·s, 10000-30000 mPa·s, and 15000-30000 mPa·s, measured at a consistency of 0.8% (w/w) and at 10 rpm.

Nanofibrillar cellulose may be or comprise non-modified nanofibrillar cellulose. The drainage of non-modified nanofibrillar cellulose is significantly faster than for example anionic grade. Non-modified nanofibrillar cellulose generally has a Brookfield viscosity in the range of 2000-10000 mPa·s, measured at a consistency of 0.8% (w/w) and at 10 rpm. However, in the present methods non-modified nanofibrillar cellulose does not crosslink efficiently because it contains a low amount of free carboxylic groups required for the crosslinking with the multivalent ions. It is preferred that the nanofibrillar cellulose has a suitable carboxylic acid content, such as in the range of 0.6-1.4 mmol COOH/g, for example in the range of 0.7-1.2 mmol COOH/g, or in the range of 0.7-1.0 mmol COOH/g or 0.8-1.2 mmol COOH/g, determined by conductometric titration.

The disintegrated fibrous cellulosic raw material may be modified fibrous raw material. Modified fibrous raw material means raw material where the fibers are affected by the treatment so that cellulose nanofibrils are more easily detachable from the fibers. The modification is usually performed to fibrous cellulosic raw material which exists as a suspension in a liquid, i.e. pulp.

The modification treatment to the fibers may be chemical, enzymatic or physical. In chemical modification the chemical structure of cellulose molecule is changed by chemical reaction ("derivatization" of cellulose), preferably so that the length of the cellulose molecule is not affected but functional groups are added to β-D-glucopyranose units of the polymer. The chemical modification of cellulose takes place at a certain conversion degree, which is dependent on the dosage of reactants and the reaction conditions, and as a rule it is not complete so that the cellulose will stay in solid form as fibrils and does not dissolve in water. In physical modification anionic, cationic, or non-ionic substances or any combination of these are physically adsorbed on cellulose surface.

The cellulose in the fibers may be especially ionically charged after the modification. The ionic charge of the cellulose weakens the internal bonds of the fibers and will later facilitate the disintegration to nanofibrillar cellulose. The ionic charge may be achieved by chemical or physical modification of the cellulose. The fibers may have higher anionic or cationic charge after the modification compared with the starting raw material. Most commonly used chemical modification methods for making an anionic charge are oxidation, where hydroxyl groups are oxidized to aldehydes and carboxyl groups, sulphonization and carboxymethylation. Chemical modifications introducing groups, such as carboxyl groups, which may take part in forming a covalent bond between the nanofibrillar cellulose and the bioactive molecule, may be desired. A cationic charge in turn may be created chemically by cationization by attaching a cationic group to the cellulose, such as quaternary ammonium group.

Nanofibrillar cellulose may comprise chemically modified nanofibrillar cellulose, such as anionically modified nanofibrillar cellulose or cationically modified nanofibrillar cellulose. In one embodiment the nanofibrillar cellulose is anionically modified nanofibrillar cellulose. In one embodiment the anionically modified nanofibrillar cellulose is oxidized nanofibrillar cellulose. In one embodiment the anionically modified nanofibrillar cellulose is sulphonized nanofibrillar cellulose. In one embodiment the anionically modified nanofibrillar cellulose is carboxymethylated nanofibrillar cellulose. The material obtained with the anionical modification of cellulose may be called anionic cellulose, which refers to material wherein the amount or proportion of anionic groups, such as carboxylic groups, is increased by the modification, when compared to a non-modified material. It is also possible to introduce other anionic groups to the cellulose, instead or in addition to carboxylic groups, such as phosphate groups or sulphate groups. The content of these groups may be in the same ranges as is disclosed for carboxylic acid herein.

The cellulose may be oxidized. In the oxidation of cellulose, the primary hydroxyl groups of cellulose may be oxidized catalytically by a heterocyclic nitroxyl compound, such as through N-oxyl mediated catalytic oxidation, for example 2,2,6,6-tetramethylpiperidinyl-1-oxy free radical, generally called "TEMPO". The primary hydroxyl groups (C6-hydroxyl groups) of the cellulosic β-D-glucopyranose units are selectively oxidized to carboxylic groups. Some aldehyde groups are also formed from the primary hydroxyl groups. Regarding the finding that low degree of oxidation does not allow efficient enough fibrillation and higher degree of oxidation inflicts degradation of cellulose after mechanical disruptive treatment, the cellulose may be oxidized to a level having a carboxylic acid content in the oxidized cellulose in the range of 0.5-2.0 mmol COOH/g pulp, 0.6-1.4 mmol COOH/g pulp, or 0.8-1.2 mmol COOH/g pulp, preferably to 1.0-1.2 mmol COOH/g pulp, determined by conductometric titration. When the fibers of oxidized cellulose so obtained are disintegrated in water, they give stable transparent dispersion of individualized cellulose fibrils, which may be, for example, of 3-5 nm in width. With oxidized pulp as the starting medium, it is possible to obtain nanofibrillar cellulose where Brookfield viscosity measured at a consistency of 0.8% (w/w) is at least 10000 mPa·s, for example in the range of 10000-30000 mPa·s.

Whenever the catalyst "TEMPO" is mentioned in this disclosure, it is evident that all measures and operations where "TEMPO" is involved apply equally and analogously to any derivative of TEMPO or any heterocyclic nitroxyl radical capable of catalyzing selectively the oxidation of the hydroxyl groups of C6 carbon in cellulose.

The modifications of nanofibrillar cellulose disclosed herein may also be applied to other fibrillar cellulose grades described herein. For example also highly refined cellulose or microfibrillar cellulose may be similarly chemically or enzymatically modified. However, there are differences for example in the final fibrillation degree of the materials.

In one example such chemically modified nanofibrillar cellulose, when dispersed in water, provides a Brookfield viscosity of at least 10000 mPa·s measured at a consistency of 0.8% (w/w) and at 10 rpm. In one embodiment such chemically modified nanofibrillar cellulose, when dispersed in water, provides a Brookfield viscosity of at least 15000 mPa·s measured at a consistency of 0.8% (w/w) and at 10 rpm. In one embodiment such chemically modified nanofibrillar cellulose, when dispersed in water, provides a Brookfield viscosity of at least 18000 mPa·s measured at a consistency of 0.8% (w/w) and at 10 rpm. Examples of anionic nanofibrillar celluloses used have a Brookfield viscosity in the range of 13000-15000 mPa·s or 18000-20000 mPa·s, or even up to 25000 mPa·s, depending on the degree of fibrillation.

In one example the nanofibrillar cellulose is TEMPO oxidized nanofibrillar cellulose. It provides high viscosity at low concentrations, for example a Brookfield viscosity of at least 20000 mPa·s, even at least 25000 mPa·s, measured at a consistency of 0.8% (w/w) and at 10 rpm. In one example the Brookfield viscosity of TEMPO oxidized nanofibrillar cellulose is in the range of 20000-30000 mPa·s, such as 25000-30000 mPa·s, measured at a consistency of 0.8% (w/w) and at 10 rpm.

In one example the nanofibrillar cellulose comprises chemically unmodified nanofibrillar cellulose. In one example such chemically unmodified nanofibrillar cellulose, when dispersed in water, provides a Brookfield viscosity of at least 2000 mPa·s, or at least 3000 mPa·s, measured at a consistency of 0.8% (w/w) and at 10 rpm.

The nanofibrillar cellulose may also be characterized by the average diameter (or width), or by the average diameter together with the viscosity, such as Brookfield viscosity or zero shear viscosity. In one example nanofibrillar cellulose suitable for use in the products described herein has an average diameter of a fibril in the range of 1-200 nm, or 1-100 nm. In one example said nanofibrillar cellulose has an average diameter of a fibril in the range of 1-50 nm, such as 2-20 nm or 5-30 nm. In one example said nanofibrillar cellulose has an average diameter of a fibril in the range of 2-15 nm, such as in the case of TEMPO oxidized nanofibrillar cellulose.

The diameter of a fibril may be determined with several techniques, such as by microscopy. Fibril thickness and width distribution may be measured by image analysis of the images from a field emission scanning electron microscope (FE-SEM), a transmission electron microscope (TEM), such as a cryogenic transmission electron microscope (cryo-TEM), or an atomic force microscope (AFM). In general AFM and TEM suit best for nanofibrillar cellulose grades with narrow fibril diameter distribution.

In one example a rheometer viscosity of the nanofibrillar cellulose dispersion is measured at 22° C. with a stress controlled rotational rheometer (AR-G2, TA Instruments, UK) equipped with a narrow gap vane geometry (diameter 28 mm, length 42 mm) in a cylindrical sample cup having a diameter of 30 mm. After loading the samples to the rheometer they are allowed to rest for 5 min before the measurement is started. The steady state viscosity is measured with a gradually increasing shear stress (proportional to applied torque) and the shear rate (proportional to angular velocity) is measured. The reported viscosity (=shear stress/shear rate) at a certain shear stress is recorded after reaching a constant shear rate or after a maximum time of 2 min. The measurement is stopped when a shear rate of 1000 $s^{-1}$ is exceeded. This method may be used for determining the zero-shear viscosity.

In one embodiment the nanofibrillar cellulose, when dispersed in water, provides a zero shear viscosity ("plateau" of constant viscosity at small shearing stresses) in the range of 1000-100000 Pa·s, such as in the range of 5000-50000 Pa·s, and a yield stress (shear stress where the shear thinning begins) in the range of 1-50 Pa, such as in the range of 3-15 Pa, determined by rotational rheometer at a consistency of 0.5% (w/w) by weight in aqueous medium. Such nanofibrillar cellulose may also have an average diameter of a fibril in the range of 1-200 nm.

Turbidity is the cloudiness or haziness of a fluid caused by individual particles (total suspended or dissolved solids) that are generally invisible to the naked eye. There are several practical ways of measuring turbidity, the most direct being some measure of attenuation (that is, reduction in strength) of light as it passes through a sample column of water. The alternatively used Jackson Candle method (units: Jackson Turbidity Unit or JTU) is essentially the inverse measure of the length of a column of water needed to completely obscure a candle flame viewed through it.

Turbidity may be measured quantitatively using optical turbidity measuring instruments. There are several commercial turbidometers available for measuring turbidity quantitatively. In the present case the method based on nephelometry is used. The units of turbidity from a calibrated nephelometer are called Nephelometric Turbidity Units (NTU). The measuring apparatus (turbidometer) is calibrated and controlled with standard calibration samples, followed by measuring of the turbidity of the diluted NFC sample.

In one turbidity measurement method, a nanofibrillar cellulose sample is diluted in water, to a concentration below the gel point of said nanofibrillar cellulose, and turbidity of the diluted sample is measured. Said concentration where the turbidity of the nanofibrillar cellulose samples is measured is 0.1%. HACH P2100 Turbidometer with a 50 ml measuring vessel is used for turbidity measurements. The dry matter of the nanofibrillar cellulose sample is determined and 0.5 g of the sample, calculated as dry matter, is loaded in the measuring vessel, which is filled with tap water to 500 g and vigorously mixed by shaking for about 30 s. Without delay the aqueous mixture is divided into 5 measuring vessels, which are inserted in the turbidometer. Three measurements on each vessel are carried out. The mean value and standard deviation are calculated from the obtained results, and the final result is given as NTU units.

One way to characterize nanofibrillar cellulose is to define both the viscosity and the turbidity. Low turbidity refers to small size of the fibrils, such as small diameter, as small fibrils scatter light poorly. In general as the fibrillation degree increases, the viscosity increases and at the same time the turbidity decreases. This happens, however, until a certain point. When the fibrillation is further continued, the fibrils finally begin to break and cannot form a strong network any more. Therefore, after this point, both the turbidity and the viscosity begin to decrease.

In one example the turbidity of anionic nanofibrillar cellulose is lower than 90 NTU, for example from 3 to 90 NTU, such as from 5 to 60, for example 8-40 measured at a consistency of 0.1% (w/w) in aqueous medium, and measured by nephelometry. In one example the turbidity of native nanofibrillar may be even over 200 NTU, for example from 10 to 220 NTU, such as from 20 to 200, for example 50-200 measured at a consistency of 0.1% (w/w) in aqueous medium, and measured by nephelometry. To characterize the nanofibrillar cellulose these ranges may be combined with the viscosity ranges of the nanofibrillar cellulose, such as nanofibrillar cellulose which, when dispersed in water, provides a Brookfield viscosity of at least 2000 mPa·s, at least 3000 mPa·s, at least 5000 mPa·s, such as at least 10000 mPa·s, for example at least 15000 mPa·s measured at a consistency of 0.8% (w/w) and at 10 rpm.

Auxiliary agents for enhancing the manufacturing process or improving or adjusting the properties of the product may be included in the nanofibrillar cellulose dispersion. Such auxiliary agents may be soluble in the liquid phase of the dispersion, they may form an emulsion or they may be solid. Auxiliary agents may be added already during the manufacturing of the nanofibrillar cellulose dispersion to the raw material or they may be added to a formed nanofibrillar cellulose dispersion. The auxiliary agents may be also added to the final product, for example by impregnating, spraying, dipping or the like method. The auxiliary agents are usually not covalently bound to the nanofibrillar cellulose, so they may be releasable from the nanocellulose matrix. A controlled and/or sustained release of such agents may be obtained when using NFC as matrix. Examples of auxiliary agents include therapeutic (pharmaceutic) and cosmetic agents and other agents affecting to the properties of the product or to the properties of the active agents, such as surfactants, plasticizers, emulsifiers or the like. In one embodiment the dispersion contains one or more salts, which may be added to enhance the properties of the final product or to facilitate water removal from the product in the manufacturing process. One example of the salt is sodium chloride. The salt may be included in an amount in the range of 0.01-1.0% (w/w) of the dry matter in the dispersion. The final product may also be dipped or soaked in a solution of sodium chloride, such as in an aqueous solution of about 0.9% sodium chloride. Desired sodium chloride content in the final product may be in the range of 0.5-1%, such as about 0.9%, of the volume of the wet product.

Hydrogels

In the final products, if the nanofibrillar cellulose is not completely dewatered, it may have a moisture content in the range of 50-99.9% (w/w), 70-99.9% (w/w), or 80-99.9% (w/w). In one embodiment the nanofibrillar cellulose is present as a gel, preferably having a moisture content in the range of 90-99.8% (w/w) or 85-97% (w/w). Moisture content may be also called as water content.

One example provides nanofibrillar cellulose in gel form, for example as a medical hydrogel. The gel may be mouldable and it may be applied onto an area requiring treatment, whereto it is attached. Also cell culture material may be provided in gel form.

Layered Products

One embodiment provides at least one layer comprising nanofibrillar cellulose and optionally other ingredients, such as non-nanofibrillar pulp or therapeutic or cosmetic agents or other auxiliary agents. The cellulose layer comprising nanofibrillar cellulose may be called herein also for example as a "layer", a "layer of membrane", a "membrane", a "film", a "sheet", a "layer comprising nanofibrillar cellulose" or a "membrane comprising nanofibrillar cellulose", or the like.

In general said layers, films, sheets, membranes or the like structures, which terms may in most cases used interchangeably, may be prepared by providing a dispersion comprising nanofibrillar cellulose and optionally other ingredients as disclosed herein, and drying or dewatering said dispersion on a support. The dispersion may be air-dried, for example at an elevated temperature. The support may include a filter or a filter may be provided in addition to the support, wherein the dewatering is carried out through the filter, which retains the nanofibrillar cellulose but allows water to pass. As a result a dried layer comprising nanofibrillar cellulose is obtained having a lowered moisture content, such as in the range of 0-20% (w/w) or 0-10%, such as 1-10%, for example 5-10% or 2-7%. In general the final moisture content of a product may be affected by the ambient atmosphere and in many cases it is therefore in the range of 5-20% (w/w), or 10-20% (w/w), unless stored in isolation, such as in a sealed package. The grammage of such layer comprising nanofibrillar cellulose may be in the range of 35-150 g/m$^2$, such as 50-110 g/m$^2$, or 60-100 g/m$^2$.

The dewatering may be carried out by applying vacuum through the filter, or by applying pressure to the layers, either from one or from two (opposite) sides, or by applying heat, or by a combination thereof. In one example vacuum is applied first, and thereafter pressure, or heat and pressure are applied by pressing with a surface, which may be heated.

This is advantageous for a product comprising nanofibrillar cellulose and having a high water content. If pressure would be applied first, the hydrogel having a high water content would tend to escape from the pressure, for example from the edges of the surface used to press the material. Therefore when vacuum is applied first, the nanofibrillar cellulose can be dewatered to a first water content, wherein the water content is low enough to allow efficient dewatering to a second water content by further applying the pressure, and optionally heat.

The product may have a density in the range of 0.8-1.2 g/cm$^3$, such as 0.80-1.10 g/cm$^3$ or 80-1.05 g/cm$^3$, for example 0.85-1.05 g/cm$^3$.

The product may have a thickness in the range of 50-1000 μm, which may include one or more layers. In one example the product has a thickness in the range of 100-1000 μm, such as 50-700 μm, 80-160 μm, 100-600 μm, 100-1000 μm, 50-250 μm, 70-200 μm, 100-150 μm, or 110-140 μm. In one example the thickness of a layer is in the range of 70-200 μm, such as 75-180 μm. Thickness may be measured as bulking thickness by ISO 534.

Tensile index of the product may be in the range of 28-95 Nm/g, such as 38-95 Nm/g, 38-80 Nm/g, or 45-77 Nm/g. The Young's modulus may be in the range of 2.5-15 GPa, for example 2.5-6 GPa, 3-14 GPa or 4-14 GPa.

The product may have an elongation (strain at break %) of 3.2% or higher, such as in the range of 3.2-6.0%, for example 3.2-4.0%. The elongation may be determined at a moisture content below 10%, such as in the range of 5-10%.

These values are especially suitable for anionic grades. A layer may comprise mainly only nanofibrillar cellulose, such as 90-99.9% (w/w), 95-99.9% (w/w), 98-99.9% (w/w), 99-99.9% (w/w) or 90-99% (w/w), 90-98% (w/w), 90-97% (w/w) or 90-95% (w/w), with the required amounts of multivalent cations and any remaining acid-releasing compounds in the range of 0.1-3% (w/w), for example 0.1-2.0% (w/w) and optionally minor amounts of other added substances. The layer comprising mainly only nanofibrillar cellulose may however contain one or more non-fibrous auxiliary agents as described herein. The nanofibrillar cellulose may be in such case the only cellulosic or fibrous material in the layer.

Multi-Layer Products

The materials and layers, films, sheets or membranes described herein may be used as membranes, layers or coatings comprising nanofibrillar cellulose when preparing multi-layered structures, which contain two or more layers. In one example existing layers, such as moisture-containing or dry or dried layers, are laminated together. In one example overlaying layers are formed in a dewatering process. In one example the multi-layered products comprise at least one gauze coated, either partly or completely, with nanofibrillar cellulose. A coating is considered as a layer.

The method for preparing a nanofibrillar cellulose product may further comprise forming the nanofibrillar cellulose as a layer or a coating in a multi-layer product, such as a product containing a layer, more particularly a fibrous layer, such as a layer of paper, board, gauze or other nonwoven. In the case of the coating only nanofibrillar cellulose may be used as the fibrillar material for preparing the coating.

It is possible to include one or more fibrous layers to the multi-layer products. The fibrous layer may contain long and/or coarse fibers, such as natural fibers and/or synthetic fibers, which may have a length of at least 5 mm. The fibrous layer may be a woven or nonwoven, and it may be for example a gauze or the like. Such products are useful in medical applications, for example as wound healing products or other products which are designed to be applied onto skin. The fibrous layer acts as a reinforcing layer and it also has an effect to other properties, such as thickness, density, permeability, pore size and the like properties of the final product. The problem with such products containing conventional nanofibrillar cellulose is that the nanofibrillar cellulose is brittle and does not provide the desired flexibility and elasticity, even if wetted, and will be easily torn. With the present crosslinked nanofibrillar cellulose it is possible to obtain multi-layer products having the desired mechanical strength. Also, the crosslinked nanofibrillar cellulose provides enhanced swelling and water retention. This is advantageous especially when the medical product is wetted, for example with saline, prior to use wherein the crosslinked material will absorb and retain more water. The high water retention helps to bind more tissue fluid and also forms a more efficient interface between the product and skin or wound.

The nanofibrillar cellulose in the following examples refers to the anionically modified crosslinked nanofibrillar cellulose described herein.

In general the medical multi-layer product comprises at least two layers. One embodiment provides a medical multi-layer product comprising
- a (first) layer comprising the nanofibrillar cellulose, preferably having a moisture content in the range of 0-20% (w/w), and
- a layer of gauze or nonwoven.

The medical multi-layer product may also comprise three layers. One embodiment provides such a medical multi-layer product further comprising a second layer comprising nanofibrillar cellulose. In one embodiment the layer of gauze is between the first layer comprising nanofibrillar cellulose and the second layer comprising nanofibrillar cellulose. The layers may also have any other order, such as a layer of gauze and two layers comprising nanofibrillar cellulose, or a first layer comprising nanofibrillar cellulose, a layer of gauze, a second layer comprising nanofibrillar cellulose and a third layer comprising nanofibrillar cellulose, or a first layer comprising nanofibrillar cellulose, a second layer comprising nanofibrillar cellulose, a layer of gauze, and a third layer comprising nanofibrillar cellulose. Two adjacent layers comprising nanofibrillar cellulose may be similar or different, for example they may have different thicknesses, concentrations, compositions, moisture contents or other properties, or they may contain different auxiliary agent(s) or one layer may not contain an auxiliary agent while the other one does, or a combination of these features. In one example one layer comprises non-modified nanofibrillar cellulose and other layer comprises modified nanofibrillar cellulose, such as anionically modified nanofibrillar cellulose. The medical multi-layer product is in general provided as sheets, which are or may be cut into desired sizes and/or shapes, for example having a width and/or length in the range of 1-20 cm, such as 1-10 cm. The final product may be provided as a dewatered product, which usually has a desired moisture content, and the product may be moisturized prior to use. In one embodiment the multi-layer products described herein do not contain any other layers, adhesives or the like between the mentioned layers, so the mentioned layers are next to each other, or in direct contact with each other, i.e. the multi-layer product consists of the mentioned layers.

In one embodiment the method comprises providing a gauze, and incorporating the nanofibrillar cellulose to the gauze. Incorporating refers to any suitable method of combining the nanofibrillar cellulose and the gauze, such as coating, layering and/or laminating. It is also possible to impregnate the gauze with the nanofibrillar cellulose. A medical product comprising a gauze is obtained.

One example provides a method for preparing a medical product, said method comprising
  providing an aqueous dispersion of nanofibrillar cellulose,
  providing a layer of gauze,
  treating the layer of gauze with the aqueous dispersion of nanofibrillar cellulose, and
  dewatering the treated gauze,
  to obtain the medical product.

The method comprises treating, such as coating, the layer of gauze with the aqueous dispersion of nanofibrillar cellulose. This may be carried out by providing the dispersion in a basin or the like and immersing or dipping the gauze into the dispersion. The gauze is kept in the dispersion for a time period suitable for letting the dispersion to treat or coat the gauze at least partially, and then the gauze is removed from the dispersion. Treating may refer to a process wherein a gauze is soaked with a dispersion comprising nanofibrillar cellulose. In practice usually the nanofibrillar cellulose does not penetrate the gauze in uniform manner but a more concentrated layer of nanofibrillar cellulose will be formed on the surface of the gauze in the final product. This process may be called coating. The nanofibrillar cellulose will bind the fibers of the gauze tightly and enhance its properties. Longer, especially non-shortened, nanofibrils may be preferred to enhance the binding. A concentrated zone or layer of nanofibrillar cellulose at a surface of the gauze enables maintaining the optimal conditions for treating the tissue specifically at the surface of the product. The inner part of the product may provide different conditions which may be helpful for example for permeability of the product. In one example the coated product contains 0.1-20% (w/w), such as 0.1-15% (w/w), for example 0.2-10% (w/w) of the nanofibrillar cellulose as the coating, 80-99.8% (w/w) of non-fibrillar fibers, 0.1-2.0% (w/w) of multivalent cations, and optionally any additional agents, such as discussed herein.

Next the wet gauze may be pressed to remove excess dispersion and liquid, and to facilitate the penetration of the dispersion into the structure of the gauze. This facilitates the even distribution of the nanofibrillar cellulose in the gauze. The properties of the gauze may however have an effect to the penetration of the nanofibrillar cellulose into the gauze, for example in the case wherein the structure or the material of the gauze is different on different sides. In one example the method therefore comprises pressing the treated gauze, which may be carried out with any suitable pressing method and/or device, to obtain the medical product.

In one example the pressing is carried out in a nip, or more particularly in a nip roll. A nip refers to the contact area where two opposing rolls meet, such as in a press or calender. Nip rolls or pinch rolls may be powered rolls and they are usually used to press two or more sheets together to form a laminated product. In one example one roll is powered and the other one is freely movable. In the examples however they may be used to press the treated gauze so the obtained product is not a laminated product. The high pressure created at the nip point brings treated gauze into intimate contact, and can squeeze out any bubbles or blisters. Nip roller units can also be used as pullers for material being pulled off of rolls or being fed between operations. Nip rolls are sometimes called squeeze rolls, pinch rolls or even wringers. Nip rolls may be used in several arrangements, such as pond size press and size press. The nip rolls may be overlapping so that the freely movable roll on top forms the pressure against the gauze fed into the nip point. The nip rolls may be for example steel rolls, which may have fine grooving. Using nip rolls was found very effective for facilitating the penetration of the dispersion into the gauze and simultaneously removing excess dispersion from the gauze. Nip rolls are very useful in an industrial scale process, wherein a long gauze sheet is fed immediately from treatment to the nip rolls and further to a next step, such as to a dewatering step.

In one example the pressing is carried out in a pond press, more particularly a pond size press. In one example the pressing is carried out in a size press.

The treated gauze is finally dewatered. In one example the method comprises dewatering the pressed gauze. This is carried out after the pressing step, or if there are several treating and pressing steps, after the last pressing step.

The dewatering may be carried out by non-contact drying, such as with an infrared dryer, floating dryer or impingement dryer, or by contact drying, such as with a press dryer, cylinder dryer or belt dryer. Air impingement drying involves blowing hot air (such as at 300° C.) in gas burners at high velocity against the wet sheet. In belt drying, the product is dried in a drying chamber by contact with a continuous hot steel band which is heated either by steam or hot gas. The water from the band is evaporated due to the heat from the band.

When drying cylinder is used the surface of the product will be smooth and the drying is cost efficient. In one example the product is dewatered in a press dryer wherein the product is placed between a Teflon plate and a cloth or fabric, and also heat is applied.

The treatment, such as coating, and the dewatering may be done once, or the steps may be repeated, if necessary to maximize saturation and/or even distribution of the dispersion in the gauze. The steps of treating and dewatering, optionally with a pressing step in between, together may be called for example as an treatment run. A specific property, such as a grammage of the product, may be desired. In such case the treatment run is repeated until the medical product has reached the desired grammage. This may be applied to any other treatment. Therefore in one embodiment the treating and dewatering are repeated at least once, i.e. the treating and dewatering are carried out at least twice. In one embodiment the treating and dewatering are carried out several times, such as 2-6 times, for example 2, 3, 4, 5 or 6 times, or more. In one embodiment the treating and dewatering are repeated until the medical product has reached a grammage in the range of 25-80 g/m2, such as 30-70 g/m2, for example 35-65 g/m2, or any other grammage disclosed herein. In one example such medical product has a grammage in the range of 45-63 g/m2. In tests medical products obtained with this method with 4-5 treatment runs had grammages in the range of 47-55 g/m2. The grammage may be also called as square mass.

One example provides a method for preparing a medical multi-layer product, said method comprising
  providing a layer comprising nanofibrillar cellulose,
  providing a layer of gauze, and
  laminating the layer comprising nanofibrillar cellulose and the layer of gauze to obtain the medical multi-layer product. The layer comprising nanofibrillar cellulose may also be called for example as a membrane layer comprising nanofibrillar cellulose or as a membrane comprising nanofibrillar cellulose. This layer may be called as a first layer comprising nanofibrillar cellulose if another further layer(s) comprising nanofibrillar cellulose is/are to be added to the product.

The method may also include the preparation of the membrane comprising nanofibrillar cellulose. One example provides a method for preparing a medical multi-layer product, said method comprising
- providing nanofibrillar cellulose,
- optionally providing non-nanofibrillar fibers, such as pulp,
- forming a dispersion of nanofibrillar cellulose optionally comprising an amount of non-nanofibrillar fibers, for example in the range of 0.1-60% (w/w) of the dry weight of total dispersion, and
- drying the dispersion on a support to form a layer comprising nanofibrillar cellulose,
- providing a layer of gauze, and
- laminating the layer comprising nanofibrillar cellulose and the layer of gauze to obtain the medical multi-layer product. The layer of gauze may be provided before drying the dispersion or it may be applied after the drying.

In one example the method further comprises providing a second layer comprising nanofibrillar cellulose, and laminating the first layer comprising nanofibrillar cellulose, the layer of gauze and the second layer comprising nanofibrillar cellulose to obtain a medical multi-layer product. In one example the layer of gauze is between the first layer comprising nanofibrillar cellulose and the second layer comprising nanofibrillar cellulose. In one example the first and the second layers comprising nanofibrillar cellulose are next to each other. The method may also comprise forming or adding the second layer comprising nanofibrillar cellulose in a similar way as the first layer is formed. The first and the second layer may be identical or they may be different.

Lamination refers to manufacturing of material in multiple layers. A laminate is a permanently assembled object by heat, pressure, welding, adhesives, or by physico-chemical adhesion e.g. hydrogen bonding. The layer comprising nanofibrillar cellulose and the layer of gauze may be attached to each other by hydrogen bonds, especially when a gauze containing natural fibers is used. A composite product is obtained. In one embodiment the laminate contains no adhesive or adhesive has not been used in the lamination.

In one example the laminating comprises stratifying or layering. A layer comprising nanofibrillar cellulose may be prepared by providing a dispersion comprising the nanofibrillar cellulose and any further ingredients, such as non-nanofibrillar fibers, one or more therapeutic or cosmetic agent(s), fillers, colorants, or other ingredients, and dewatering the dispersion to a desired moisture or dry content with a suitable dewatering method. The dewatering may be carried out through a gauze to attach the layer comprising nanofibrillar cellulose to the gauze. Any of the dewatering methods described herein may be used. The dispersion may be provided as a gel, such as a hydrogel.

One example provides a method for preparing a medical multi-layer product, the method comprising
- providing a filter, such as a filter fabric,
- providing an aqueous dispersion comprising nanofibrillar cellulose, such as a gel,
- providing a gauze,
- applying the dispersion onto the filter,
- applying the gauze onto the dispersion, and
- dewatering the structure through the filter to obtain the medical multi-layer product.

One example provides a method for preparing a medical multi-layer product, the method comprising
- providing a filter, such as a filter fabric,
- providing a gauze,
- providing an aqueous dispersion comprising nanofibrillar cellulose, such as a gel,
- applying the gauze onto the filter,
- applying the dispersion onto the gauze, and
- dewatering the structure through the filter to obtain the medical multi-layer product.

Further layers of dispersions comprising nanofibrillar cellulose may be formed. The further layers may have the same composition as the first layer, or they may be different. For example one layer may contain therapeutic or cosmetic agent and another layer does not, or it may contain a different therapeutic or cosmetic agent.

One example provides a method for preparing a medical multi-layer product, the method comprising
- providing a filter, such as a filter fabric,
- providing a gauze,
- providing a first dispersion comprising nanofibrillar cellulose, such as a gel,
- providing a second dispersion comprising nanofibrillar cellulose, such as a gel, which may be same or different than the first dispersion comprising nanofibrillar cellulose,
- applying the first dispersion onto the filter,
- applying the gauze onto the first dispersion,
- applying the second dispersion onto the gauze, and
- dewatering the structure through the filter to obtain the medical multi-layer product.

When a gauze is between two layers both comprising nanofibrillar cellulose, the nanofibrillar celluloses in the two layers may contact each other through the gauze thereby adhering strongly together. The gauze is completely covered with the layers comprising nanofibrillar cellulose so the gauze will not be adhered to a skin or to a wound in the skin during the use. Also the product may be applied onto the skin with either side towards the skin. However, one side of the product may contain a thicker layer of nanofibrillar cellulose which is meant to be applied against the skin. This side may be indicated in the product, for example by marking the side or the other side with text, figures, colours or the like.

The dewatering may be carried out by applying vacuum through the filter, or by applying pressure to the layers, either from one or from two (opposite) sides, or by applying heat, or by a combination thereof. The dewatering methods of a membrane comprising nanofibrillar cellulose described herein may be applied to the layering process. The filter fabric may be as described herein. The filter is impermeable to the fibrillar cellulose, i.e. it has such a pore size that the fibrillar material does not pass the filter.

The gauze as used herein refers to any suitable gauze, such as a fabric, a cloth or the like material comprising fibers. The gauze may be woven or nonwoven, sterile or nonsterile, plain or impregnated, or fenestrated (perforated or with slits), or a combination thereof.

The gauze may be woven. By one definition a woven gauze is a thin, translucent fabric with a loose open weave. In technical terms a woven gauze is a weave structure in which the weft yarns are arranged in pairs and are crossed before and after each warp yarn keeping the weft firmly in place. The gauze may comprise natural fibers, semi-synthetic fibers or synthetic fibers, such as viscose, rayon, polyester and the like, or combinations thereof, for example a viscose-polyester mixture. When used as a medical dressing, gauze may be made of cotton. The gauze may also act as a pad of a patch. In one embodiment the gauze is viscose-polyester gauze, for example non-woven. Such a non-woven gauze is very porous and permeable and it is moderately elastic providing irreversible elongation in one direction.

Preferably the gauze is nonwoven. Nonwoven gauze comprises fibers pressed together to resemble a weave, which provides improved wicking and greater absorbent capacity. Compared to woven gauze, this type of gauze produces less lint and has the benefit of leaving fewer fibers behind in a wound when removed. Examples of nonwoven gauze dressings include gauzes made of polyester, viscose, or blends of these fibers which are stronger, bulkier, and softer than woven pads. Instead of a gauze it is also possible to use any other suitable nonwoven. The embodiments and examples disclosed herein for gauze may be also applied to nonwovens in general.

The gauze may comprise absorbing material, for example to enhance the ability of the medical product to absorb exudate, to soak up blood, plasma, and other fluids exuded from the wound and containing them in one place. The gauze may also stem bleeding and to help sealing a wound. The gauze may also absorb a therapeutic agent or other agent.

In one embodiment the gauze comprises natural fibers or natural-fiber-based material, such as cotton, cellulose, linen, silk or the like. Natural fibers provide free hydroxyl groups which helps attaching the gauze to the layer(s) comprising nanofibrillar cellulose via hydrogen bonds. Also semi-synthetic fibers may provide free hydroxyl groups, such as viscose.

The gauze should be highly permeable allowing fluids to pass through. The gauze is not a filter and it does not limit the flow through of most macromolecules. The gauze may not be used as a filter for dewatering a dispersion comprising nanofibrillar cellulose. The gauze may be porous and/or it may be fenestarated having perforations or slits or the like. A paper or cardboard is not a gauze. More particularly paper is not suitable as paper does not provide high enough tear strength in such grammages or thicknesses which would be suitable for the multi-layer products. The same applies to cardboard or other similar cellulosic products. However, paper, cardboard or the like cellulosic materials may be suitable for some specific applications. In one example the gauze is non-cellulosic. The gauze may comprise long fibers having an average fiber length of at least 5 mm, at least 7 mm, or at least 10 mm, for example in an amount of at least 15% (w/w) of the total gauze, or at least 20% (w/w) or at least 25% (w/w).

In one example the gauze is resilient. Many natural, semi-synthetic or synthetic fibers are resilient. However, in one example the gauze is rigid providing non-resilient properties, for example when it comprises cotton. The gauze may provide reinforcing properties, for example to enhance the tear strength of the multi-layer product.

Tear strength (tear resistance) is a measure of how well a material can withstand the effects of tearing. More specifically it measures how well a material resists the growth of any cuts when under tension. Tear resistance may be measured by the ASTM D 412 method (the same may be used to measure tensile strength, modulus and elongation). Also a tear index may be presented, wherein tear index=tear strength/grammage, and it is usually measured in mNm$^2$/g.

The gauze may have a tear strength in the range of 1500-2000 mN, such as 1700-1900 mN. The gauze may have a tear index in the range of 50-60 mNm$^2$/g. Tear index may be measured with ISO 1974. The tensile strength of the multi-layer product may be more than 1.5 kN/m, such as in the range of 1.5-3.0 kN/m, such as 1.6-2.0 kN/m. Tensile strength may be measured by ISO 1924-3. The gauze may have a grammage in the range of 20-50 g/m$^2$, for example in the range of 20-40 g/m$^2$ or 20-30 g/m$^2$. Grammage may be measured by ISO 536. The gauze may have a density for example in the range of 270-350 g/cm$^3$, such as in the range of 290-330 g/cm$^3$. Also a bulk may be presented as cm$^3$/g, measured by ISO 534.

A layer of gauze, such as a dry gauze, may have a thickness in the range of 100-1000 µm, such as 100-200 µm, 150-200 µm, 200-300 µm, 300-400 µm, 400-500 µm, 500-600 µm, 600-700 µm, 700-800 µm, 800-900 µm or 900-1000 µm. However, thicker gauzes may also be used, for example up to 2000 or 3000 µm. In one embodiment the thickness of the gauze is in the range of 100-200 µm, such as 100-120 µm, 120-140 µm, or 140-160 µm or 160-190 µm. However, when the gauze was combined with the layer(s) comprising nanofibrillar cellulose, the total thickness of the final dry multi-layer product could be lower than the thickness of the dry gauze alone.

The medical multi-layer product may have a thickness in the range of 100-1000 µm. Even thicker products may be prepared, for example having a thickness of about 1500 µm, 2000 µm, 2500 µm or 3000 µm. In one embodiment the medical multi-layer product has a thickness in the range of 100-500 µm, such as 100-400 µm, 100-300 µm, 100-200 µm, or 120-180 µm, for example 120-150 µm, 120-140 µm or 130-140 µm. In general the thickness of the gauze layer in the final product may be in the range of 100-1000 µm, such as 100-200 µm, 150-200 µm, 200-300 µm, 300-400 µm, 400-500 µm, 500-600 µm, 600-700 µm, 700-800 µm, 800-900 µm or 900-1000 µm. In one example the thickness of the gauze layer in the product is in the range of 100-160 µm, such as 140-160 µm, for example about 150 µm. In one example the thickness of the gauze layer in the product is in the range of 100-120 µm, for example about 105 µm. Thickness may be measured as bulking thickness by ISO 534.

In the multi-layer products the layers comprising nanofibrillar cellulose may have a variety of thicknesses depending on desired properties of the product, such as absorption capacity, stiffness, etc. If there are more than one such layers the layers may each have different thicknesses. For example the layer which is in contact with the skin during the use may have higher thickness than the layer which is at the other side of the gauze. In one embodiment the layer has a thickness in the range of 5-60 µm. The thickness of a layer which is in contact with the skin may be in the range of 20-60 µm or 20-50 µm, for example 30-40 µm. Usually if a layer has a thickness over 60 µm the stiffness increases and the layer may not be suitable for all the uses described herein. However, in some cases it may be possible to use thicker layer, such as up to 100 µm, or even up to 150 or 200 µm, for example in the range of 40-80 µm, 50-100 µm, 20-200 µm, 50-150 µm, 50-200 µm or 100-200 µm. The thickness of a layer which is at the other side of the product may be in the range of 5-10 µm. This layer may be thinner because one of its main functions is to seal the product in such way that the gauze is not exposed. The thickness of a layer, for example a nanofibrillar layer, may be determined from a final product for example by dying and/or microscopically.

In one embodiment the multi-layer product comprises a first layer comprising nanofibrillar cellulose having a thickness in the range of 20-60 µm, a layer of gauze having a thickness in the range of 140-160 µm, and a second layer comprising nanofibrillar cellulose having a thickness in the range of 5-10 µm.

In one embodiment the multi-layer product comprises a first layer comprising nanofibrillar cellulose having a thickness in the range of 20-60 µm, a layer of gauze having a thickness in the range of 100-120 µm, and a second layer comprising nanofibrillar cellulose having a thickness in the range of 5-10 µm.

With a reinforcing gauze the tear index of the medical structure is remarkably higher. In one embodiment the medical multi-layer product has a tear index in the range of 18-100 mNm$^2$/g. In one embodiment the medical multi-layer product has a tear index in the range of 20-70 mNm$^2$/g. The tear index may be different in one direction and in a perpendicular direction, which may be affected by the properties of the gauze. For example a gauze may have different properties to the perpendicular directions, which may be called as machine direction and cross direction.

In one embodiment the medical multi-layer product has a grammage in the range of 50-100 g/m$^2$. In one embodiment the medical multi-layer product has a grammage in the range of 60-80 g/m$^2$, for example in the range of 64-75 g/m$^2$.

In one embodiment the medical multi-layer product has a density in the range of 300-800 kg/m$^3$, such as 350-700 kg/m$^3$, for example 450-650 kg/m$^3$. The density may be measured as apparent bulking density by ISO 534.

Medical Products

The present application provides medical products, which may be applied onto the skin or other tissue of a target or a subject, such as a patient or a person, human or animal, suffering from a condition. The medical products may be provided as gels, patches, plasters, bandages or the like, which may be applied onto a wound or onto damaged area or onto an area or a target requiring treatment. The medical products may be provided as sheets cut into suitable size(s) to be applied to a target, or the product may be provided as sheets or the like which may be cut into desired sizes). The present application also provides methods for preparing the medical products.

The term "medical" refers to a product or use wherein the product, i.e. a product comprising the nanofibrillar cellulose (NFC) of the embodiments, is used or is suitable for medical purposes or for scientific purposes, for example for treatment or for research. A medical product may be designed, packed, labelled, indicated and/or instructed to be used for medical or scientific purpose, i.e. the medical product may contain any suitable indication that it is for medical purpose, such as text and/or picture in a packing, a wrapping, a coating, a label or the like. A medical product may be sterilized, or it is sterilizable, before and/or after immobilizing the bioactive molecule, for example by using temperature, pressure, moisture, chemicals, radiation or a combination thereof. The product, preferably the hydrogel with the attached molecule(s), may be for example autoclaved, or other methods using high temperature may be used, in which cases the product should tolerate high temperatures over 100° C., for example at least 121° C. or 134° C. In one example the product is autoclaved at 121° C. for 15 minutes. It is also desired that a medical product is pyrogen free and it does not contain undesired protein residues or the like. A medical product is preferably non-toxic to the target. Also UV sterilization may be used.

The medical products described herein may be used in several applications. One specific field is medical applications, wherein the materials are applied on living tissue, such as skin. The structures may be used in medical products, such as patches, dressings, bandages, filters and the like. The medical products may also be therapeutic products, such as therapeutic patches containing medicament. In general the surface of the product comprising nanofibrillar cellulose will be in contact with the skin during the use. A surface of nanofibrillar cellulose may provide advantageous effects when it is in direct contact with the skin, for example it may promote healing of a wound or other damage on a skin, and simultaneously it provides the bioactive substances from the medical product to the skin.

Certain advantageous properties of the products, such as medical products, described herein include flexibility, elasticity, rigidity and remouldability. If the nanofibrillar cellulose contains moisture, it may also show suitable permeability. These properties are useful for example when the product is used as a dressing for healing wounds, or in other medical applications, such as for delivering therapeutic or cosmetic agents.

Flexibility is a feature which is desired in many applications, such as in medical applications. Flexible patches and dressings comprising nanofibrillar cellulose are useful for applying onto skin, for example for covering wounds and other damages or injuries, such as burns.

The medical products may contain only one layer of nanofibrillar cellulose, or they may contain one or more additional layers, which may be nanofibrillar cellulosic layers and/or other layers. In case of one layer the density of the layer may be relatively low, such as in the range of 0.8-1.2 g/cm$^3$, however the layer exhibits good mechanical properties, such as high elasticity and elongation at break. Therefore the materials are suitable to be used as single-layer products.

The term "wound" as used herein refers to any damages, injuries, diseases, disorders or the like on a tissue, such as skin, including open or closed wounds, wherein the healing of the wound is desired and may be promoted with the product described herein. The wound may be clean, contaminated, infected or colonized, wherein especially in the latter cases a therapeutic agent, such as an antibiotic, may be administered. Examples of open wounds include abrasions, avulsions, incisions, lacerations, puncture wounds and penetration wounds. Examples of closed wounds include hematomas, crush injuries, sewn wounds, grafts and any skin conditions, diseases or disorders. Examples of conditions, diseases or disorders of the skin include acne, infections, vesiculobullous diseases, cold sore, cutaneous candidiasis, cellulitis, dermatitis and eczema, herpes, hives, lupus, papulosquamous, urticaria and erythema, psoriasis, rosacea, radiation-related disorders, pigmentation, mucinoses keratosis, ulcer, atrophy, and necrobiosis, vasculitis, vitiligo, warts, neutrophilic and eosinophilic diseases, congenital, neoplasms and cancer, such as melanomas and tumours of epidermis or dermis, or other diseases or disorders of epidermis and dermis.

A medical product comprising a therapeutic agent may be provided, wherein the nanofibrillar cellulose product contain(s) one or more therapeutic agent, such as a medicament or drug. Also the term pharmaceutical agent may be used interchangeably instead of the term therapeutic agent. Such agents are active or effective agents, which are usually present in effective amounts. Such an agent may be provided in a predetermined amount, for example in an amount configured to provide a desired dose of the agent during a certain time period, and/or configured to provide a desired effect on the target, such as skin or other tissue. The content of the therapeutic agent in a layer or the product may be for example in the range of 0.1-5%. When the therapeutic agent is included in a layer comprising nanofibrillar cellulose, a sustained, a delayed or a prolonged release of the agent may be provided. In such case the layer comprising nanofibrillar cellulose may contain a portion of moisture to enable permeability of the agent. The moisture content of a layer comprising nanofibrillar cellulose and therapeutic agent may be in the range of 0-10%, such as in the range of 5-7%. The therapeutic agents may be present in water-soluble form, fat-soluble form or in an emulsion, or in another suitable form.

Examples of therapeutic agents which may be administered by using the medical products described herein include antibiotics, pain relievers, such as lidocaine; nicotine; opioids, such as fentanyl or buprenorphine; hormones, such as estrogen, contraceptives or testosterone; nitroglycerin; scopolamine; clonidine; antidepressants, such as selegiline; ADHD medication, such as methylphenidate; vitamins, such as B12 or cyanocobalamin; 5-hydroxytryptophan; Alzheimer's medication, such as rivastigmine; acne medication; antipsoriatics, glucocorticoids such as hydrocortisone; or any other medication for treating diseases or disorders of a skin. Therapeutic agents may be used for example in medical patches, which may be used on healthy skin or on damaged skin, to provide a prolonged, delayed, sustained or extended release of the therapeutic agent from the patch, for example during a period of several hours, for up to 6, 12, 24 or even 48 hours.

One embodiment provides the medical product comprising antibiotic agent. Such a product is especially suitable for treating wounds, wherein the wound treating properties are combined with antibiotic properties which prevents infections caused by harmful microbes in the wound. Examples of suitable antibiotics include especially topical antibiotics, such as bacitracin, erythromycin, clindamycin, gentamycin, neomycin, polymyxin, mupirocin, tetracycline, meclocycline, (sodium) sulfacetamide, benzoyl peroxide, and azelaic acid, and combinations thereof. Also other types of antibiotics, such as systemic antibiotics, may be provided, for example penicillins, such as phenoxymethylpenicillin, flucloxacillin and amoxicillin; cephalosporins, such as cefaclor, cefadroxil and cephalexin; tetracyclines, such as tetracycline, doxycycline and lymecycline; aminoglycosides, such as gentamicin and tobramycin; macrolides, such as erythromycin, azithromycin and clarithromycin; clindamycin; sulphonamides and trimethoprim; metronidazole and tinidazole; quinolones, such as ciprofloxacin, levofloxacin and norfloxacin.

Antibiotics may be also used for treating acne, for example clindamycin, erythromycin, doxycycline, tetracycline etc. Also other agents may be used, such as benzoyl peroxide, salicylic acid, topical retinoid medicines, such as tretinoin, adapalene or tazarotene, azelaic acid, or androgen blockers such as spirolactone. Psoriasis may be treated for example with steroids, such as corticosteroids, moisturizers, calciprotriene, coal tar, vitamin D, retinoids, tazatorene, anthralin, salisylic acid, methotrexate, or cyclosporine. Insect bites or poison ivy exposure may be treated with agents such as hydrocortisone, emu oil, almond oil, ammonia, bisabolol, papain, diphenylhydramine, jewelweed axtract or calamine. Some of these or other treatment agents may be also categorized as cosmetic agents.

One embodiment provides a medical product, such as a dressing, a patch or a filter, comprising the medical product described herein.

One example provides the medical product for use for treating and/or covering skin wounds or other damages. One example provides such a medical product for use as a dressing or a patch, or in a dressing or a patch, for treating and/or covering skin wounds or other damages.

One example provides such a medical product for use for treating and/or covering skin wounds covered with a graft, such as a skin graft. One embodiment provides such a medical product for use as a dressing or a patch, or in a dressing or a patch, for treating and/or covering skin wounds covered with a graft, such as a skin graft.

A dressing is a sterile pad or compress applied to a wound to promote healing and/or prevent further harm. A dressing is designed to be in direct contact with the wound, as distinguished from a bandage, which is most often used to hold a dressing in place. Some organizations classify them as the same thing (for example, the British Pharmacopoeia) and the terms are used interchangeably by some people. Dressings are frequently used in first aid and nursing.

One example provides the medical product for use for administering therapeutic agent. In such case the medical product may be provided as such or for example in a patch. One or more therapeutic agent(s) may be included, for example impregnated, in the product as described herein, and the administration to a patient may be dermal or transdermal. One example provides a method for administering therapeutic agent, the method comprising applying the medical multi-layer product comprising one or more therapeutic agent onto skin. The agent(s) are to be administered to a target, which may be a human or animal target, which may be in need of the agent(s).

One embodiment provides a cosmetic product, such as a dressing, a mask or a patch, comprising the medical product. Such a product may be called also as a cosmetic product. The product may be provided in various shapes, for example a mask may be designed to fit onto face, for example below eye or onto chin, nose or forehead. One embodiment provides the medical product for use as a cosmetic product. The product may be used for releasing one or more cosmetic agent(s) to the user, such as to the skin of the user. Such a cosmetic product may comprise one or more cosmetic agent(s). Cosmetic agent(s) may be included, for example impregnated, in the product, such as into a layer comprising nanofibrillar cellulose, wherefrom they will be released or delivered. The content of a cosmetic agent in a layer may be for example in the range of 0.1-5%. The cosmetic agents may be present or provided in the product similarly as explained above for therapeutic agents, and vice versa. The cosmetic use may be analogous to medical use described herein, especially the administering of therapeutic agent. Cosmetic agents may be used also for cosmetically treating skin diseases or disorders, such as those mentioned herein. Such cosmetic products may be used for example for treating pimples, acneic skin, brown sports, wrinkles, oily skin, dry skin, aged skin, spider veins, after sun erythemas, black circles etc. Examples of cosmetic patches include skin cleansers, such as pore cleansers, blackhead removers, stretching stripes, short-term patch-like masks, short-term treatment patches and overnight treatment patches.

Examples of cosmetic agents include forms of vitamins and precursors thereof, such as vitamin A; for example retinoids, such as retinaldehyde (retinal), retinoic acid, retinyl palmitate and retinyl retinoate, ascorbic acid, alpha-hydroxy acids such as glycolic acid and lactic acid; glycols; biotechnology products; keratolytics; amino acids; antimicrobials; moisturizers; pigments; antioxidants; plant extracts; cleansing agents or make-up removers; anti-cellulite agents such as caffeine, carnitine, *Ginkgo biloba* and horse-chestnut; conditioners; fragrances such as aromatherapy agents and perfumes; humectants such as urea, hyaluronic acid, lactic acid and glycerine; emollients such as lanolin, triglycerides and fatty acid esters; FR scavengers, singlet oxygen scavengers, superoxide scavengers or hydrogen peroxide scavengers, such as ascorbic acid (vitamin C), glutathione, tocopherol (vitamin E), carotenoids, coenzyme Q10, bilirubin, lipoic acid, uric acid, enzyme mimetic agents, idebenone, polyphenols, selenium, spin traps such as phenyl butyl nitrone (PBN), protein methionine groups, superoxide dismutase, catalase, selenium peroxidases, heme oxygenases etc. or combinations thereof. The cosmetic agents may be present in water-soluble form, fat-soluble form or in an emulsion, or in another suitable form.

One example provides a method for cosmetically treating skin, the method comprising applying the medical product, preferably containing one or more cosmetic agent, described herein onto skin.

The products containing effective or active agents, such as therapeutic or cosmetic agents, may contain one or more layers of nanofibrillar cellulose. The agent may be contained in one layer only, or it may be contained in two or more layers. Two or more layers may also contain a different agent in each layer. Two or more different agents may be all therapeutic agents or they may be all cosmetic agents or they may comprise both therapeutic and cosmetic agents, for example a first therapeutic agent in a first layer and a second therapeutic agent in a second layer, or a therapeutic agent in a first layer and a cosmetic agent in a second layer. Further, a first layer containing no such agent may be provided, which layer is to be applied against the skin, and a second layer next to the first layer may contain the agent. Alternatively, the first layer may contain the agent and the second layer next to the first layer does not contain any agents. With such arrangements it is possible to control for example the delivery rate or order of the agents.

A "patch" as used herein refers to a medical or cosmetic product which may be applied onto skin. Examples of patches include dermal patch and transdermal patch. A dermal patch or skin patch is a medicated adhesive patch that is placed on the skin to deliver a medication into the skin. A transdermal patch is a medicated adhesive patch that is applied on the skin to deliver a specific dose of medication through the skin and into the bloodstream. In one example this promotes healing to an injured area of the body. A patch may contain a release liner, which protects the patch during storage and is removed prior to use, and/or adhesive for adhering the patch to the skin, and/or backing for protecting the patch from the outer environment. Examples of release liners include paper-based liners, such as glassine paper, densified Kraft super-calendered paper, clay-coated paper, silicone-coated paper and polyolefine-coated paper; plastic based liner, such as polystyrene, polyester, polyethylene, cast polypropylene and polyvinyl chloride; and composite material liners based on the combination of several films. Adhesive layers may contain for example pressure sensitive adhesive (PSA).

One embodiment provides the medical product or the medical product described herein packed in a separate packing, usually in a sealed packing. Separate packings may be provided as a series of packings. Usually such packed products are provided as sterilized.

One embodiment provides a kit comprising the medical product, the medical product or the cosmetic product described herein, wherein the kit may contain one or more of the packed medical products. The kit may also contain other materials or equipment, such as a container containing saline solution or the like for pretreating the product(s) prior to use.

The packages, kits or the like described herein may contain written and/or illustrated instructions or a link to such instructions or other indication how to use or what is the purpose of the product included in the package, kit or the like. The instructions may for example indicate that the product is for medical or cosmetic use or purpose, and the instructions may include instructions of for example how to apply the product, or when to use the product, for example as explained herein.

One example provides a method for treating a patient, the method comprising applying the medical product onto skin of the patient, which may be a human or animal patient. One example provides a method for treating skin wounds or other damages or injuries, the method comprising applying the medical product onto the wound, damage, or injury. One specific example provides a method for treating skin wounds covered with a graft, such as a skin graft, for example a mesh graft or a full thickness graft, the method comprising applying the medical product onto the graft.

Grafting refers to a surgical procedure to move tissue from one site to another on the body, or from another person, without bringing its own blood supply with it. Instead, a new blood supply grows in after it is placed. Autografts and isografts are usually not considered as foreign and, therefore, do not elicit rejection. Allografts and xenografts are recognized as foreign by the recipient and are rejected.

Skin grafting is often used to treat skin loss due to a wound, burn, infection, or surgery. In the case of damaged skin, it is removed, and new skin is grafted in its place. Skin grafting can reduce the course of treatment and hospitalization needed, and can also improve function and appearance. There are two types of skin grafts: Split-thickness skin grafts (epidermis+part of the dermis) and full-thickness skin grafts (epidermis+entire thickness of the dermis).

A mesh graft is a full- or partial-thickness sheet of skin that has been fenestrated to allow drainage and expansion. Mesh grafts are useful in many locations on the body because they conform to uneven surfaces. They can be placed in locations that have excessive motion because they can be sutured to the underlying wound bed. Additionally, their fenestrations provide outlets for fluid that may accumulate beneath the graft, which helps reduce tension and the risk of infection and improve vascularization of the graft.

It was found out in the clinical tests that the medical product comprising nanofibrillar cellulose attaches to a graft area and acts as a protective layer. As the graft heals, the product forms a scab-like structure together with the graft. The properties of the medical product comprising nanofibrillar cellulose promote the healing, and the membrane with the formed dry scab will come loose in similar way as a regular scab behaves in normal wound healing process.

Before applying the medical product onto skin the product may be pretreated i.e. moisture or wetted, in general with an aqueous solution. The moisturizing or wetting may be carried out for example by using water or regular physiological saline solution, which is usually a solution of 0.90% w/w of NaCl, having an osmolality of about 308 mOsm/l. Other types of aqueous solutions may also be used, such as saline solutions with different concentrations. Moisturizing or wetting the material enhances contact with the skin and the moldability of a sheet of material.

The present application also provides use of the products as medical products in any of the medical applications disclosed herein.

Cell Culture Materials

Different cell culture materials may be prepared by using the method disclosed herein. These materials may be used for culturing different types of cells in different methods. The nanofibrillar cellulose product acts as a matrix for cell culture or delivery. One advantage of the nanofibrillar cellulose material is that the dimensions of the fibrillar network of cellulose nanofibers is very close to natural ECM network of collagen nanofibers. Furthermore, cellulose nanofiber is non-animal based material, so there is no risk for disease transfer. Currently, most of the commercial products are isolated from animals. With the present materials it is possible to obtain a transparent and porous matrix for the cells, and the mass production of the material is easy compared to the alternatives.

The cell proliferation may be almost double in case of cellulose nanofibers compared to cells only. Cells can be controlled on NFC hydrogels for long time, for example for 2-7 days. Cells use cellulose nanofiber matrix as a growing platform and form clusters, which indicate the usefulness of cellulose nanofibers as 3D cell culture scaffold. Cells can grow as layers within the CNF gel. Cellulose nanofibers have negligible fluorescence background. Cellulose nanofiber hydrogel has optimal elasticity, stiffness, shear stress, mechanical adhesion and porosity to be used as 3D and 2D cell culture matrix. Cell growth or cell culture media containing NFC may be used for maintaining and growing cells as well as for transferring cells.

One embodiment provides a cell culture or cell delivery composition, material or matrix comprising the nanofibrillar cellulose product, such as in a form of a hydrogel or a membrane in wet state. The cell culture or cell delivery material may be provided at a first water content, and aqueous liquid may be added to the material to obtain a second water content. The wet state may refer to the first or the second water content. The second water content may be the water content the cell culture or cell delivery composition has during the use, such as during culturing or delivering the cells. The first water content may be the water content of the product or material described herein, such as water content below 20%. The second water content may be a water content of 30% or more, such as 50% or more, 60% or more, or 70% or more, which may be considered as hydrogels. The added aqueous liquid may be cell culture medium. The cell culture medium is an aqueous medium used in the cell culture.

The cell culture or cell delivery material may be in the form of a membrane or in the form of separate bodies. The cells may be cultured on the surface of the membrane, for example at a first location. The membrane may be then transferred to another location, which may be for example a patient. For example specific cells may be administered to a wound or another damaged tissue, such as skin. Also the separate bodies may be used in similar way.

One embodiment provides a cell culture or cell delivery material comprising living cells and the cell culture or cell delivery material forming a hydrogel. The cell culture or cell delivery material together with the cells forms a cell culture matrix. The cells may be present in the material in a three-dimensional or two-dimensional arrangement. The cells may be eukaryotic or prokaryotic cells, such as animal or human cells, for example stem cells.

One embodiment provides a method for preparing the cell culture or cell delivery material, the method comprising providing the nanofibrillar cellulose product, and mixing with aqueous liquid, such as water. A mixture comprising the material is obtained. The mixture may be further combined and/or mixed with one or more auxiliary agents, such as pharmaceuticals, growth factors, nutrients, pH adjusting agents and the like.

One embodiment provides a method for removing the nanofibrillar cellulose product from a cell culture material, the method comprising
  providing cell culture material containing cells;
  diluting said cell culture material with aqueous or non-aqueous liquid;
  optionally centrifuging the cell culture material to sediment the cells and cell aggregates;
  removing nanofibrillar cellulose product, for example by decantation.

One embodiment provides a method for removing the nanofibrillar cellulose product from a cell culture material, the method comprising
  providing cell culture material containing cells;
  contacting the cell culture material with an enzyme capable of degrading the nanofibrillar cellulose material;
  optionally centrifuging the cell culture material to sediment the cells and cell aggregates;
  removing nanofibrillar cellulose product, for example by decantation. Preferably nanofibrillar cellulose product to be removed is enzymatically degraded to obtain at least partly and preferably mostly degraded nanofibrillar cellulose product.

One embodiment provides microbiological use of the nanofibrillar cellulose product or the material for laboratory and/or industrial purposes as a medium or a compound of a media for maintaining cells in vitro.

One embodiment provides a method for culturing cells, the method comprising
  providing cells;
  contacting the cells with the cell culture or cell delivery material, such as to form a matrix;
  culturing the cells in the cell culture or cell delivery material, such as within said matrix, for example in a three-dimensional or two-dimensional arrangement.

One embodiment provides a three-dimensional discontinuous entity for culturing of cells comprising an aqueous medium and hydrogel bodies comprising the nanofibrillar cellulose product suspended in the aqueous medium. The aqueous medium may be a cell culture medium comprising at least one nutrient source and at least one component required for sustaining undifferentiated, differentiating or differentiated cell growth. In one embodiment the hydrogel bodies are interconnected. The hydrogel bodies may have a water content in the range of 1-90%, more particularly 1-50%, or 1-20%. If the material is highly dewatered, it may have a water content in the range of 0-20%, 0-10% or 1-10%, and instead of hydrogel bodies the material may be provided as nanofibrillar cellulose bodies.

In one embodiment the total volume of the hydrogel bodies from total volume of the three-dimensional discontinuous entity is in the range of 10-99% (v/v), such as 50-95% (v/v).

The yield stress of the three-dimensional discontinuous entity is lower than the yield stress of the corresponding continuous hydrogel in the same conditions, such as 1-95% of the yield stress of the corresponding continuous hydrogel in the same conditions.

One embodiment provides a discontinuous three-dimensional entity and a method for producing such, wherein the method for manufacturing a three-dimensional discontinuous entity for culturing cells comprises
  providing the nanofibrillar cellulose product in a form of
    i) a homogeneous hydrogel;
    ii) a combination of the homogeneous hydrogel with an aqueous medium; and/or iii) dehydrated gel bodies or dry granulated nanofibrillar cellulose product hydrated in an aqueous medium; and mixing at conditions favouring mechanical disruption of the homogeneous structure of the hydrogel to obtain a suspension of hydrogel bodies as a three-dimensional discontinuous entity.

One embodiment provides a cell culture matrix. One embodiment provides a cell culture and a method for preparing a cell culture, comprising providing the cell culture material disclosed herein, providing cells, providing an aqueous cell culture medium, and mixing them to obtain a cell culture.

One embodiment provides an article and use of the article for cell culture the article comprising a substrate having a surface;

a three-dimensional discontinuous entity comprising an aqueous medium and hydrogel bodies comprising the nanofibrillar cellulose product suspended in the aqueous medium, or a three dimensional discontinuous entity comprising an aqueous medium and hydrogel bodies comprising the nanofibrillar cellulose product suspended in the aqueous medium in a dehydrated form;

and optionally at least one component selected from the group consisting of a cell culture medium, extra cellular matrix components, serum, growth factors, proteins, antibiotics, preservatives. The articles comprising the three-dimensional discontinuous entities may be any article suitable for culturing cells, such as cell culture bottles, plates and dishes, multiwall culture plates, microtiter plates, high throughput plates and the like. Preferably, the articles are cell culture grade.

One embodiment provides use of the three-dimensional discontinuous entity above for culturing cells or tissues.

One embodiment provides a method for transporting cells, comprising transporting the cells in the three-dimensional discontinuous entity as disclosed herein.

One embodiment provides a method for three-dimensional or two-dimensional culturing of cells or tissues comprising providing the three-dimensional discontinuous entity, inoculating at least one cell with the three-dimensional discontinuous entity; and culturing to obtain a cell mass.

One embodiment provides a kit comprising a first and a second container, the first container comprising the three-dimensional discontinuous entity or the three-dimensional discontinuous entity in dehydrated form such as dry powder, concentrated granulate, or concentrated hydrogel body, and the second container comprising cellulase.

The term "three-dimensional discontinuous entity" refers to a system having three-dimensionally discontinuous structure. Said entity comprises an aqueous medium and hydrogel bodies comprising cellulose nanofibrils and/or derivatives thereof suspended in the aqueous medium.

"Discontinuous" refers to the heterogeneous structure of the entity or to interruptions in the physical continuity within the entity, for example interruptions in the aqueous medium by hydrogel bodies or interruptions in and/or between hydrogel bodies by the aqueous medium. In general the discontinuous material may comprise a plurality of separate, including partly separate, bodies, domains, granules, particles and the like, which may have substantially spherical, elliptical, or the like, or uneven shape. The plurality of bodies, domains, granules, particles and the like may be also partly interconnected.

"A hydrogel body" and "a hydrogel domain" refer to an aliquot, a division, a domain, a fraction, a portion or a dose of a hydrogel. The hydrogel body may have a well-defined, indefinite, symmetrical or asymmetrical shape.

"Suspended" or "suspension" when used in context of three-dimensional discontinuous entity or hydrogel bodies refers to a heterogeneous mixture of an aqueous medium and hydrogel wherein the hydrogel may be present as separate and/or interconnected hydrogel bodies.

"Interconnected" and "interconnection" when used in context of hydrogel bodies refers to a system where the hydrogel bodies are in contact with each other. The contact may be a direct connection between the hydrogel bodies or the hydrogel bodies may be loosely connected. When the homogeneous structure of the hydrogel is broken e.g. by mixing, the resulting discontinuous structure is characterized by hydrogel bodies of different sizes and forms. The resulting system may contain aqueous cavities between interconnected gel bodies or the loosely connected hydrogel bodies may "float" in the aqueous medium having contacts with each other. The hydrogel bodies may be indirectly connected via e.g. cells or other components present in the system.

The term "cell culture matrix" refers to a system comprising cells and/or tissue and the three-dimensional discontinuous entity, the cells and/or tissue being present at least partially embedded in said entity in a three-dimensional or two-dimensional arrangement. Three-dimensional and two-dimensional in context of cell cultures refers to the way the cells are arranged, for example 3D may refer to cluster or spheroid-like arrangement and 2D to single or layered arrangement.

The term "cell culture" or "culturing of cells" refers to maintaining, transporting, isolating, culturing, propagating, passaging and/or differentiating of cells or tissues. Cells may be in any arrangement such as individual cells, monolayers, cell clusters or spheroids or as a tissue.

The term "cell culture matrix" refers to material configured for cell culturing and providing a growth matrix that increases the available attachment surface for the adherence of the cells so as to mimic the infrastructure of the tissue.

The term "article for cell culture" refers to any article suitable for cell culture including single and multi-well plates, such as 6, 12, 96, 384, and 1536 well plates, jars, petri dishes, flasks, multi-layered flasks, beakers, plates, roller bottles, slides, such as chambered and multichambered culture slides, tubes, cover slips, bags, membranes, hollow fibers, beads and microcarriers, cups, spinner bottles, perfusion chambers, syringes, bioreactors, and fermenters.

"In dehydrated form" refers to form of the material in which some but not necessarily all water is removed from the material in question. Thus, the term dehydrated encompasses e.g. concentrated slurries, granules, flakes, and powders. The dehydrated material may have a water content in the range of 0-90%, such as 0-80%, 0-50%, 1-50%, 1-40%, 1-30%, 1-20%, 10-50%, 10-40%, 10-30%, or 1-10%.

The term "kit" refers to a combination of articles or containers that facilitate a method, assay, or manipulation of the three-dimensional discontinuous entity or articles for cell culture using such. Kits may contain instructions describing how to use the kit (e.g., instructions describing the methods of the invention), cartridges, mixing stations, chemical reagents, as well as other components. Kit components may be packaged together in one container (e.g. box, wrapping, and the like) for shipment, storage, or use, or may be packaged in two or more containers.

The three-dimensional discontinuous entity, cell culture matrix or article may further comprise suitable additives selected from the group consisting of nutrients, buffering agents, pH indicators, extra cellular matrix components, serum, growth factors, antibiotics, preservatives and proteins.

The fraction volume of the gel bodies comprising the three-dimensional discontinuous entity may vary between 50% and 99% of the total volume of the three-dimensional discontinuous entity and, accordingly, the local CNF concentration may be higher or lower than that of the total entity. The fraction volume of the gel bodies may be for example 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%. The fraction of the gel bodies may be qualitatively determined readily e.g. by inspection under microscope or by sedimentation analysis.

Any cell can be cultured using the present three-dimensional discontinuous entity and cell culture materials or articles. Eukaryotic cells, such as animal cells e.g. mammalian cells, plant cells, algal and fungal cells, can be grown using the three-dimensional discontinuous entity and article, as well as prokaryotic cells such as bacterial cells. The cells may be human primary cells from any normal or abnormal tissue type, human secondary cell lines from any tissue type, human immortalized cell lines, and human cancer cells from either primary tumor or metastatic tumor. The cells may be any undifferentiated cells, such as pluripotent, multipotent, oligopotent or unipotent cells including embryonic stem cells, nonhuman embryonic stem cells, induced pluripotent stem cells, somatic multipotent stem cells, somatic pluripotent stem cells, tissue specific stem cells, mesenchymal stem cells, or progenitor cells, neural stem cells, hepatic stem cells, or endothelial stem cells. A suitable cell to be cultured using the present three-dimensional discontinuous entity or article is a human or non-human ESC. A human or nonhuman iPSC is also suitable. In one aspect the cell to be used in the products according to the invention is any stem cell which is derived from established hES cell lines available to the public or which is obtained by a method which does not exclusively involve destruction of human embryos from which the said product is derived. In one aspect more than one cell type of different origin is cultured as a coculture.

The three-dimensional discontinuous entity, article, material and methods provide culturing of cells for a long time. When undifferentiated cells are cultured, they can be propagated and passaged several times while the pluripotency of the cell mass is maintained. This allows increasing the pluripotent cell mass into larger quantities required e.g. for therapy.

The cells cultured using the present three-dimensional discontinuous entity, material, article and methods can be transported in the culture system or article without need for freezing the cells before transportation. In the present systems and applications the cultured cells can be transported directly after culturing them in the three-dimensional discontinuous entity, material or article e.g. at +37° C. without additional steps and culturing of the transported cells can be continued using the same system and apparatus which was used in the transportation. The transported cells can be harvested from the matrix, and the culturing may be continued in 2D or 3D culture.

Depending on the cell line and the intended use of the cultured cell, the culturing may be carried out 2D or 3D. The cells are dispersed or inoculated on or in the three-dimensional discontinuous entity or article allowing 2D or 3D growth of cells on the hydrogel bodies and penetration of the propagating cells and extracellular structures of the cultured cells inside the hydrogel bodies.

The removal of cellulose nanofibers may be carried out for example with enzyme mixtures comprising one or more enzymes, such as some or all necessary enzymes for partial or total degradation of cellulose molecules as well as other wood derived components in it, such as hemicelluloses. Examples of the enzymes include exocellulases, such as exoglucanases, and endocellulases, such as endoglucanases. Further examples include designed enzyme mixtures for the NFC in question and commercially available cellulase-hemicellulase preparations. The composition of the mixture can vary depending on the chemical composition of the raw material used for production of that NFC. For example when birch pulp is used for production of NFC the mixture includes at least intact endo- and exocellulases or parts thereof, endo-xylanases and 13-D-glycosidases and 13-D-xylosidases. For hydrolysis of softwood-derived NFC the mixture needs to be supplemented at least with endomannanases and 13-D-mannosidases. The benefit of designed mixtures pooled from purified enzyme components is that they do not contain additional proteins or other unwanted components, such as side activities, debris from the cultivation organism or residues from culture broth, which is often the case for commercial enzyme preparations. Especially harmful is, if the preparation contains proteases, which might attack on the cultured cell surfaces. Commercial enzyme mixtures designated for total hydrolysis of plant based materials can also be used in hydrolysis of NFC, but more preferably after at least crude purification step, such as gel filtration or dialysis. Regardless of the enzyme preparation, either a designed or commercial mixture, the components are selected so that they can optimally hydrolyse NFC for example in respect of pH, temperature and ionic strength. Commercial preparations are available, which are acting either in the acidic pH values (pH 3.5-5) or basic pH values (pH 6-8) and at temperatures from room temperature up to 60-80° C. Very often the cells are grown at 37° C., which is an optimal temperature for the most cellulases and hemicellulases. The cultured cell lines may be also genetically engineered to produce the needed enzyme protein(s) into the culture system.

The three-dimensional discontinuous entity is obtainable by a method comprising steps of providing the nanofibrillar cellulose product in a first aqueous medium to provide a hydrogel, and mixing said hydrogel with a second aqueous medium to obtain a suspension of hydrogel bodies in the second aqueous medium. The first and the second aqueous medium can be of same medium type, but also different, the first medium being e.g. water and the second cell culture medium. The three-dimensional discontinuous entities can be made also from concentrated cellulose nanofibril hydrogels or from dry cellulose nanofibrils by granulating the concentrated hydrogel or dry cellulose nanofibrils to obtain granules, hydrating the granules in an aqueous medium, and mixing the hydrated granules, optionally adding aqueous medium, to obtain a suspension of hydrogel bodies. The discontinuous structure of the hydrogel can be verified e.g. by simple microscopic analysis or yield stress determination and comparison with the homogeneous hydrogel having the corresponding NFC concentration.

Discontinuous gel structures can be made also from concentrated (e.g. 10-30% w/w) or even from dry cellulose nanofiber products. When using dry or concentrated materials, the sample is first granulated to an appropriate size (e.g. 0.1-2 mm), hydrated in water or in cell culture medium, and then activated into either continuous or discontinuous form using appropriate methods. Spray dried particles, having an average diameter in the range of 2-20 micrometers, can be also used as a starting material. The controlled porosity in these kinds of discontinuous gels is dependent on particle size and the total concentration, i.e. distance between the swollen gel domains or gel bodies The products described herein may be provided as packed in a packing containing one or more of the products. The products may be packed in sealed packings, for example to keep them uncontaminated and to maintain moisture content, such as when the products is provided as dried or at a certain water content. When a product provided as dried or dewatered is used, it may be moisturized to a desired moisture content prior to use.

EXAMPLES

Example 1: Diffusion-Aided Bridging

Films were made of mixtures of chemical pulps and catalytically oxidized NFC. The films were prepared on a support which was then soaked in solutions of $CaCl_2$) and $MgCl_2$ to exchange the sodium ions originally present in the film to divalent metal cations. Without binding to any specific theory, it was assumed that the electrostatic bonding between the anionic pulp fibers and the fibril network would promote internal bonding that would then reflect positively on the film properties. The immersion of the wet film into aqueous $CaCl_2$) or $MgCl_2$ solidified the film with time. When the solidified films were dried with an excess of the salt, elastic, skin-like materials were formed. Rewetting in water and redrying the materials produced paper-like films with improved mechanical properties in comparison with films prepared without the divalent cation salts. Scanning electronic microscopy (SEM) imaging of the fracture surfaces provided support for the increased internal film strength by the divalent cations.

Materials

Never-dried (ND) and dried bleached hardwood (birch) kraft pulps (BHKP) were obtained from a Finnish pulp mill and were used without any further treatment. BHKP was heat treated in laboratory to produce HT BHKP with tailored fiber properties (Table 1). Oxidized NFC was made of BHKP as described in Saito, T., Kimura, S., Nishiyama, Y. & Isogai, A. Cellulose nanofibers prepared by TEMPO-mediated oxidation of native cellulose. Biomacromolecules 8, 2485-2491 (2007). Hardwood celluloses were oxidized by a 2,2,6,6-tetramethylpiperidine-1-oxyl radical (TEMPO)-mediated system, and highly crystalline and individualized cellulose nanofibers, dispersed in water, were prepared by mechanical treatment of the oxidized cellulose/water slurries.

The carboxylate content of the NFC was 0.8 mmol/g. The NFC was stored in the $Na^+$ form at pH 5.5 at 2.5% consistency. The average width of the fibrils was about 7 nm measured by transmission electron microscopy. Magnesium chloride ($MgCl_2$) and calcium chloride ($CaCl_2$)) were purchased from Sigma-Aldrich and used as received.

TABLE 1

Fiber properties of the never dried BHKP (ND BHKP), BHKP and heat treated BHKP (HT BHKP) samples.

| Pulp | Fiber length (mm) | Curl index (%) | Kinks ($m^{-1}$) |
|---|---|---|---|
| ND BHKP | 1.09 | 8.7 | 550 |
| BHKP | 1.05 | 10.9 | 810 |
| HT BHKP | 0.91 | 41.3 | 4160 |

Preparation of Nanofibrillar Cellulose Films

A mixture of oxidized NFC (15 g), pulp (15 g of ND BHKP, BHKP or HT BHKP) and water was homogenized for 20 min at 3% overall consistency using an Ultra Turrax mixer (D125 Basic, IKA) to obtain a uniform hydrogel. Then 25 g cellulose hydrogel was applied over a Teflon mould (60 mm×140 mm) by a rod coating setup. The mould was transferred into a 1000 ml bath of 0.3 M salt solution ($MgCl_2$ or $CaCl_2$)) that was gently mixed for 3 h. With time the hydrogel solidified, and the film separated from the support. The solid film was then transferred into a water bath (1000 ml) and kept there under gentle mixing for 15 min or 1 h to remove the excess of the salt. The film was dried at 23° C. and 50% relative humidity (RH) for 24 h. The air-dry film was soaked again in the water bath for 15 min or 1 h, after which the drying at 23° C. and 50% RH was repeated.

Analyses

For the analysis of their metal content (Ca, Mg, Na), 150 mg samples of the films were mixed with 10 ml nitric acid in Teflon vessels. The vessels were heated in a microwave oven (Milestone, Ethos) for 1 h at 200° C. After cooling the vessels, the samples were diluted with 50 ml Milli-Q water. The content of sodium was determined using F-AAS (AA240, Varian). The calcium and magnesium contents were analysed with ICP-OES (DV7100, Perkin Elmer).

Tensile testing of the films was carried out at 23° C. and 50% RH using an Instron 4204 Universal Tensile Tester equipped with a 50 N load cell, a gauge length of 40 mm. The speed of the cross-head speed was 1 mm/min. The film specimens were 10 mm×50 mm in size and they were equilibrated for at least 3 h at 23° C. and 50% RH before the mechanical testing. The film thickness was estimated by a thickness gauge under a low and constant pressure, according to the international standard regarding thickness of paper and board (ISO 534). The film density was calculated from the actual dimensions and weights of the dry films after conditioning them at 23° C. and 50% RH. This apparent density measurement was repeated at least three times for each sample. The moisture content of the conditioned films was calculated from the weight before and after heating at 100° C. for 3 h.

SEM was applied for imaging of the films at 10,300× and 35,490× magnifications (Sigma VP Field-Emission Scanning Electron Microscope, FE-SEM. Zeiss). Wet films of HT BHKP/fibrillar cellulose were immersed in 0.3 M $MgCl_2$ or 0.3 M $CaCl_2$) solutions for 3 h before freeze drying of the films. The corresponding films were also imaged after immersing in water and drying in air. In this case the dry films were immersed in liquid nitrogen and ruptured to reveal the inside structure of the films. The operating voltage was 3 kV and the working distance was approximately 2.5 mm. Prior to imaging, the samples were sputtered with gold and palladium.

Results and Discussion

The principle of fixing wet films of oxidized NFC and pulp with divalent cations is illustrated in FIG. 1. A homogeneous suspension of NFC ($Na^+$ form) and pulp is first spread on a support and then immersed in an aqueous solution of a divalent metal salt, such as $CaCl_2$) or $MgCl_2$. The sodium counter ions in NFC/pulp are substituted for $Ca^{2+}$ or $Mg^{2+}$ by the actions of diffusion, ion exchange and the Donnan effect that favors bonding of divalent cations on the anionic NFC/pulp. The divalent cations bridge the carboxylate groups between the fibrils and fibers which leads to solidification of the film within a time required for completing the diffusion over the film thickness. The excess of salt is then removed from the wet film by diffusion in pure water.

When a wet NFC/pulp film on a support was immersed in water, it dispersed the NFC/pulp mixture. On the contrary, soaking in aqueous $CaCl_2$ or $MgCl_2$ started to solidify the film immediately. Typically 1-3 h were required to complete the solidification depending of several factors, such as the film thickness and the concentration of the salt solution. The second treatment in water did not change the appearance of the wet, solidified film. Drying of the films in air left them moist, elastic and skin-like material. Typically softeners, like glycerol or other polyalcohols, may provide a similar elasticity of NFC/pulp films. Obviously, some chloride was still present in the structure since rewetting and redrying of the films made them drier and more paper-like. After the rewetting the calcium content of the $CaCl_2$) treated films was 160-230 mmol/kg in comparison with their carboxylate content of ca. 450 mmol/kg, approaching a 1:2 stoichiometric ration between $Ca^{2+}$ and the carboxylate groups (Table 2). On the contrary, the second immersion in water removed most of $Mg^{2+}$ ($MgCl_2$ treated films) and $Na^+$ (untreated films) from the films.

TABLE 2

Metal contents of NFC/pulp films after 1 h treatment in excess of water.

| Pulp | Na (mmol/kg) | Ca (mmol/kg) | Mg (mmol/kg) |
|---|---|---|---|
| ND BHKP ($Na^+$) | 13 | — | — |
| ND BHKP ($Ca^{2+}$) | 5 | 160 | — |
| ND BHKP ($Mg^{2+}$) | 5 | — | 50 |
| BHKP ($Na^+$) | 9 | — | — |
| BHKP ($Ca^{2+}$) | 5 | 180 | — |
| BHKP ($Mg^{2+}$) | 6 | — | 50 |
| HT BHKP ($Na^+$) | 14 | — | — |
| HT BHKP ($Ca^{2+}$) | 6 | 230 | — |
| HT BHKP ($Mg^{2+}$) | 6 | — | 60 |

The binding of metal cations of the treated NFC/pulp depends on several factors, such as the original carboxylate content, the ion-exchange and washing procedures, and the strength of the metal carboxylate interaction. The $pK_a$ values of C6-carboxyl groups are 2.8-3.7, and therefore, at the pH 5.5 applied, most of the carboxyl groups were dissociated and associated with the metal cations ($Na^+$, $Ca^{2+}$ or $Mg^{2+}$). On the other hand, as the data of Table 2 shows, soaking the films in a large excess of water, shifted the equilibrium to favour the undissociated carboxylic acid form, depending on the metal salt used. The sorption of $Ca^{2+}$ on oxidized nanofibrillated cellulose is stronger than that of $Mg^{2+}$ after soaking in aqueous nitric acid ($HNO_3$) or aqueous sodium nitrate ($NaNO_3$).

Figure 2A:
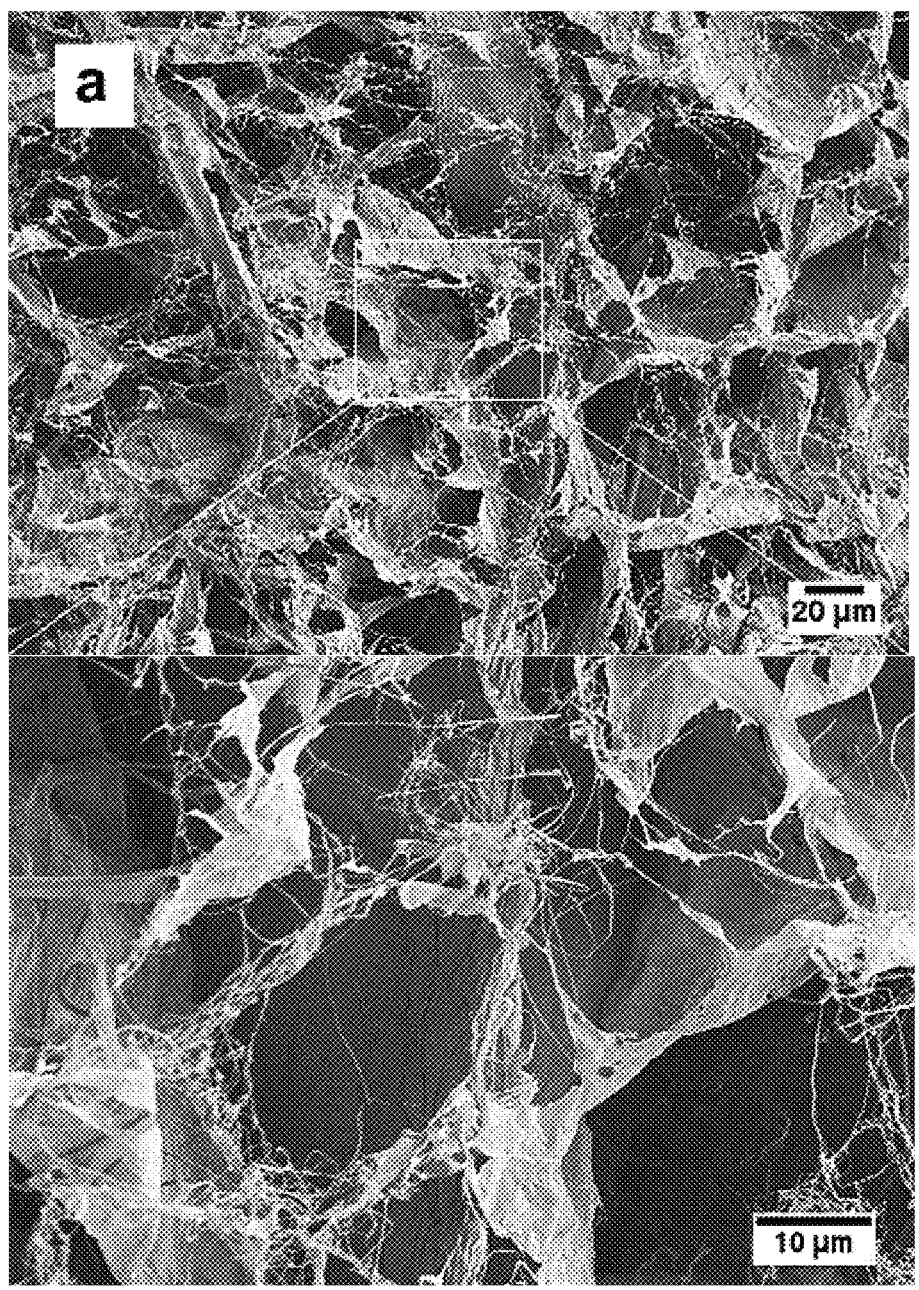
FIG. 2 shows SEM images of freeze-dried HT BHKP/NFC films (surfaces) before (a) and after soaking in aqueous $CaCl_2$) (b) and $MgCl_2$ (c).
Figure 2B:
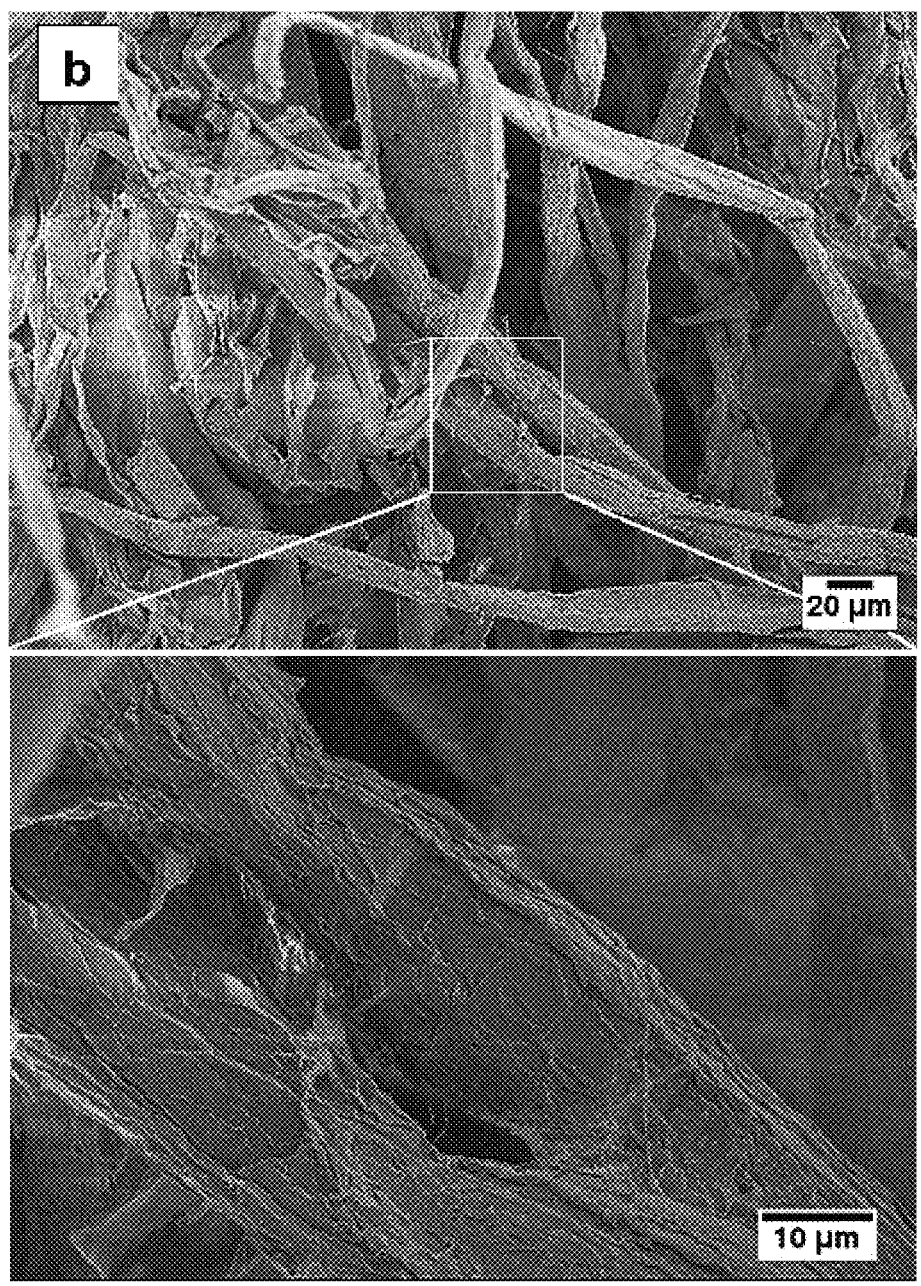
Figure 2C:
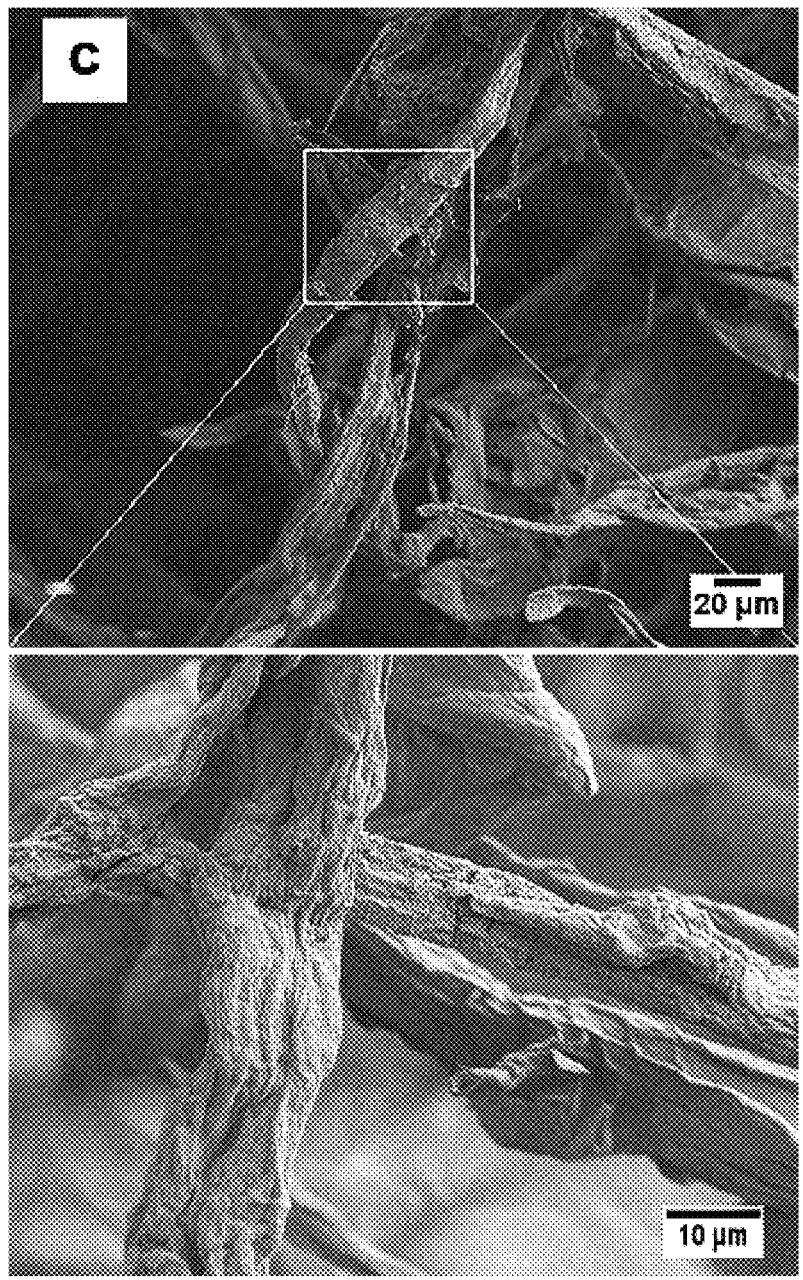

Freeze-drying of wet NFC/pulp films in $Na^+$ form and their subsequent SEM imaging visualized the porous, fibrillar and membrane-type structures that are typical of NFC (FIG. 2a). These structures dominated the images over the pulp fibers that were hardly visible. In contrast, when the films were freeze dried right after their solidification in aqueous $CaCl_2$) or $MgCl_2$, the pulp fibers dominated the images (FIGS. 2b and c). Obviously, NFC was attached on the surfaces of the pulp fibers that formed a porous network in this case.

Figure 3:
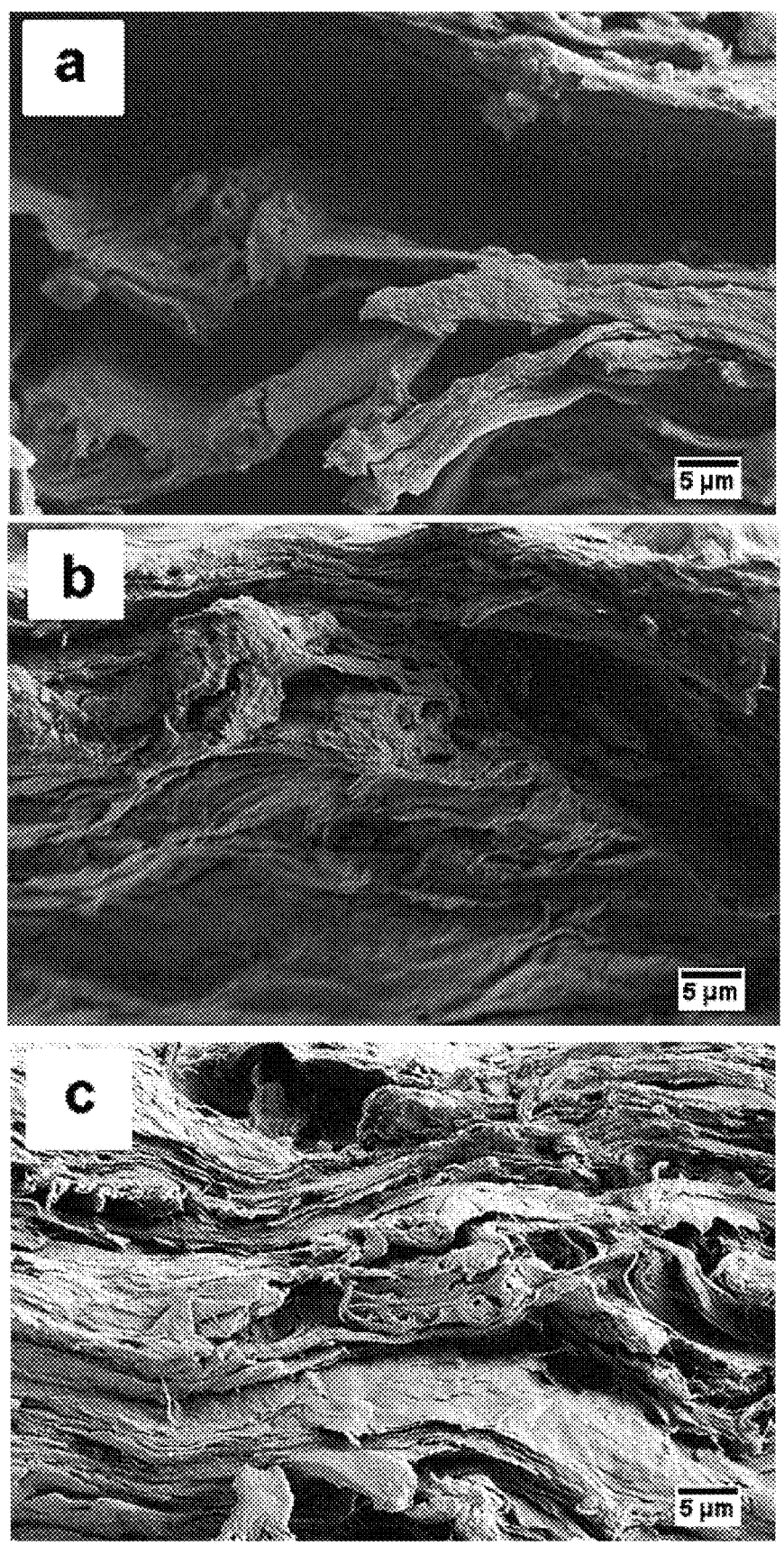
FIG. 3 shows SEM images of the freeze-fractured surface of HT BHKP/NFC films in $Na^+$ (a), $Ca^{2+}$ (b), and $Mg^{2+}$ (c) forms.

Another set of SEM images were collected from the solidified NFC/pulp films after soaking in water, drying, rewetting and redrying (FIG. 3). The films were freeze-fractured and the images were taken on the fracture surfaces representing cross sections of the films. The cross sections of the films in $Ca^{2+}$ and $Mg^{2+}$ form revealed a consolidated structure with repeating <0.5 μm thick horizontal lamella (FIGS. 3b and c). No fiber separation was observed at the fracture surfaces. In contrast, the film in $Na^+$ form obviously delaminated during the freeze-fracture demonstrating a lower internal strength (FIG. 3a). In this case, individual fibers became visible in the fracture surface although the intact films in $Na^+$ form were, in average, denser than the films in $Ca^{2+}$ and $Mg^{2+}$ form (Table 3). The consolidation of the sheets occurred only in the vertical direction as their lateral dimensions remained practically constant during the drying.

Figure 4:
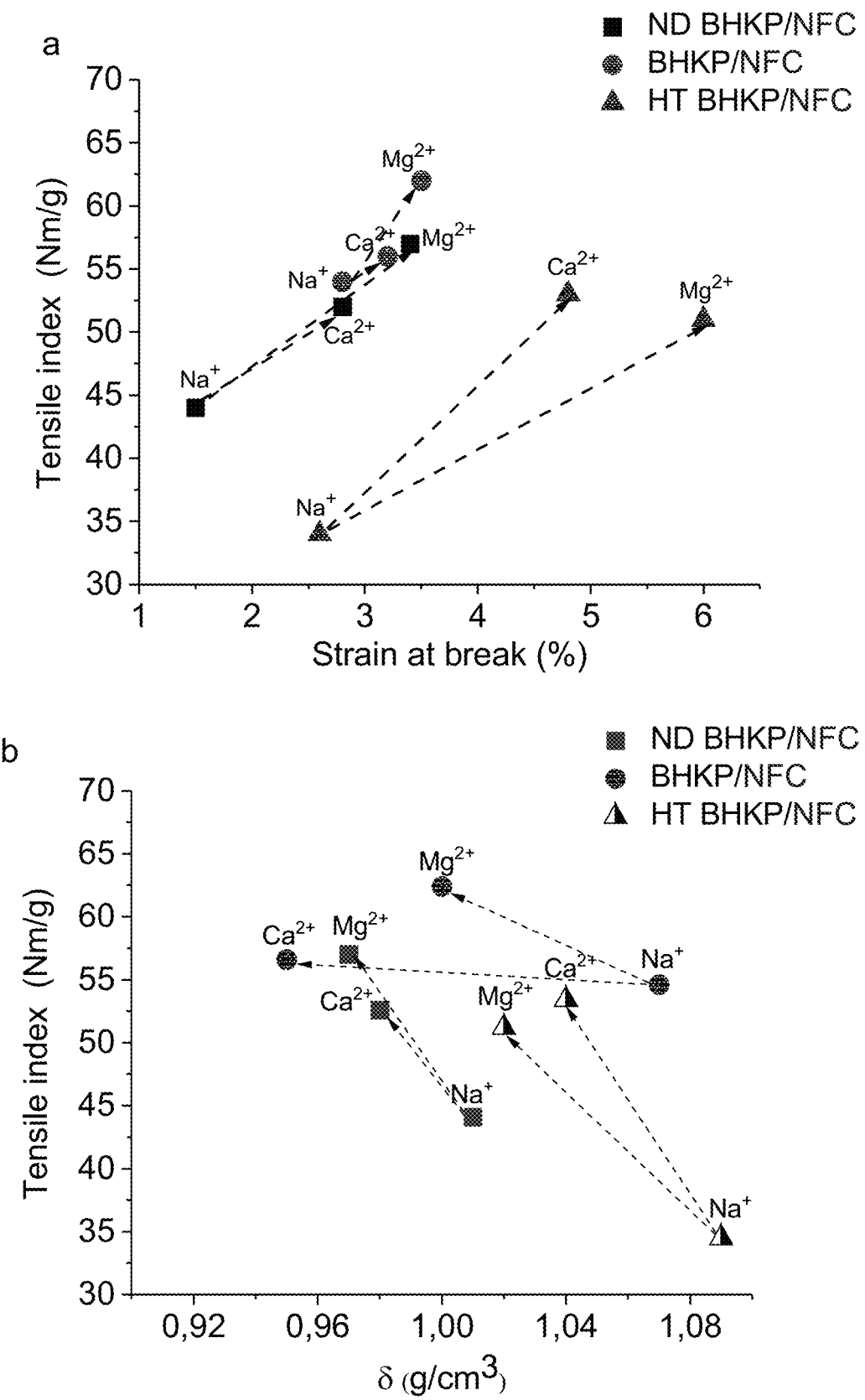
FIG. 4 shows tensile index against strain at break (a) and density (b) of NFC/pulp films tested at 23° C. and 50% RH.

In addition to their lower density, the films in $Ca^{2+}$ and $Mg^{2+}$ form had higher elastic moduli and tensile indices than the films in $Na^+$ form did demonstrating again the positive effect of the divalent cations on internal strength of the material (FIG. 4b). The treatment of the films with $CaCl_2$) and $MgCl_2$ also increased their strain at break (FIG. 4a). The increase was largest with HT BHKP the fibers of which were curlier than those of the untreated kraft pulps (Table 1). The counter ion did not significantly affect the moisture content of the sheets under the constant conditions, 23° C. and 50% RH, applied in testing of the film properties (Table 3). The strain percentage refers to percentage elongation at break, also known as fracture strain, which is the ratio between changed length and initial length after breakage of the test specimen.

TABLE 3

Properties of NFC/pulp films tested at 23° C. and 50% RH.

| Pulp | Tensile index (Nm/g) | Strain (%) | Thickness (μm) | Young's modulus (GPa) | Moisture content, % | Density (g/cm³) |
|---|---|---|---|---|---|---|
| ND BHKP ($Na^+$) | 44.1 ± 3 | 1.5 ± 0.07 | 130 ± 9 | 6.4 ± 0.5 | 8.3 ± 1.9 | 1.01 ± 0.04 |
| ND BHKP ($Ca^{2+}$) | 52.6 ± 1 | 2.8 ± 0.35 | 98 ± 3 | 12.4 ± 1.2 | 8.5 ± 0.25 | 0.98 ± 0.04 |
| ND BHKP ($Mg^{2+}$) | 57 ± 4 | 3.4 ± 0.42 | 114 ± 8 | 8.0 ± 0.3 | 8.0 ± 0 | 0.97 ± 0.09 |
| BHKP ($Na^+$) | 54.6 ± 0.2 | 2.8 | 92 ± 5 | 7.1 ± 0.2 | 9.0 ± 0 | 1.07 ± 0.05 |
| BHKP ($Ca^{2+}$) | 56.6 ± 3 | 3.2 ± 0.21 | 84 ± 5 | 9.7 ± 0.6 | 5.3 ± 0.2 | 0.95 ± 0.06 |

TABLE 3-continued

Properties of NFC/pulp films tested at 23° C. and 50% RH.

| Pulp | Tensile index (Nm/g) | Strain (%) | Thickness (μm) | Young's modulus (GPa) | Moisture content, % | Density (g/cm³) |
|---|---|---|---|---|---|---|
| BHKP ($Mg^{2+}$) | 62.4 ± 3 | 3.5 ± 0.28 | 87 ± 4 | 10.5 ± 0.11 | 5.2 ± 0 | 1.00 ± 0.04 |
| HT BHKP ($Na^+$) | 34.5 ± 5 | 2.6 ± 0.6 | 124 ± 5 | 3.3 ± 0.1 | 8.5 ± 1.9 | 1.09 ± 0.09 |
| HT BHKP ($Ca^{2+}$) | 53.4 ± 5 | 4.8 ± 0.8 | 136 ± 5 | 4.0 ± 0.6 | 7.4 ± 0.98 | 1.04 ± 0.06 |
| HT BHKP ($Mg^{2+}$) | 51.2 ± 0.7 | 6.0 ± 0.05 | 167 ± 12 | 3.3 ± 0.26 | 8.6 ± 1.49 | 1.02 ± 0.03 |

Conclusions

Exchange of $Na^+$ to $Ca^{2+}$ or $Mg^{2+}$ as the counter ion of wet films of oxidized NFC and pulp increases the internal strength of the films in wet and dry state. In the presence of an excess of the divalent metal salt, such as $CaCl_2$ or $MgCl_2$, drying of the film forms an elastic, skin-like material. Removal of the excess of the salt before drying leads to a paper-like film the properties of which depend also on the type of the pulp used. Curly pulp fibers provide films with high elongation at break.

Example 2: Time-Triggered Bridging

This example presents a method to improve the mechanical properties of the cellulose films by crosslinking $Ca^{2+}$/oxidized NFC using precipitated $CaCO_3$ on heat treated bleached kraft hardwood pulp (PCC-HT BKHW) without flock formation. Thin sheets can be produced adding acetic anhydride ($Ac_2O$) in cellulose gel that contains PCC-HT BKHWP and NFC. In this procedure, adding $Ac_2O$ led to a reduction pH from 7.3 to 4.8 via acid hydrolysis and releasing $Ca^{2+}$ cations. Consequently, free calcium cations can bond with the carboxyl groups on NFC, which formed paper-like films. It was possible to prevent the formation of undesirable flock during the acid hydrolysis, thereby accelerating the process and making it suitable for the industrial scale. The measurement of tensile properties revealed that the tensile index and breaking strain increased with the addition of $Ac_2O$ to cellulose gels with different ratios of NFC and PCC-HT BKHWP. This approach represents an efficient and inexpensive method to improve the mechanical properties of packaging materials by cross-linking $Ca^{2+}$ with carboxyl groups in fiber networks.

Materials

HT BKHW and TEMPO-oxidized NFC ($Na^+$ form) were obtained from a Finnish pulp mill and were used without any further treatment. The consistency of the NFC dispersion was 2.5%, its sodium carboxylate content was 0.8 mmol/g and pH 5.5. The carboxylate content of the oxidized NFC was 0.8 mmol/g. The average width of the fibrils was about 7 nm measured by transmission electron microscopy. Lime from Lhoist, Ltd. (France) and acetic anhydride from VWR were used without further purification. Pure $CO_2$ gas was from AGA (Finland).

PCC Co-Precipitation onto Pulp Fibers

Calcium carbonate ($CaCO_3$) can be produced by carbonation in two steps. First, water is added to calcium oxide (lime) to obtain calcium hydroxide ($Ca(OH)_2$). This process is called lime slaking. Then, the slaked lime reacts with carbon dioxide and forms precipitated calcium carbonate (PCC).

For this study, slaked lime ($Ca(OH)_2$) was produced mixing lime and water with a high-shear mixer for 10 min at 50° C. Then, the solid content of HT BKHW pulp was adjusted around 25±2% and mixed at moderate rotational speed in a KM098 Kenwood mixer. After 5 min mixing, slaked lime was added to the pulp in a proportion of 1:9. Then, the suspension was mixed again at moderate speed for 10 min. After mixing, the homogeneity of $Ca(OH)_2$ was tested by measuring the pH of 4 different samples. An acceptable homogeneity was achieved with a pH of 12.6±0.2. PCC co-precipitation was accomplished feeding $CO_2$ gas into the covered mixing chamber at a flow rate of 0.3 Nl/min. The $CO_2$ dissolves in the aqueous phase and forms carbonic acid, which reacts with the $Ca(OH)_2$ to form $CaCO_3$. The end of the reaction was considered to occur when the pH reached 7.7±0.1. The gas flow was stopped and mixing continued for another 30 minutes. The final pH was 8.3±0.1. The PCC content determined by standard ISO 2144:1997(E) was 7.59±0.13 wt %.

Preparation of NFC Films

A mixture of NFC and PCC-HT BKHWP and water was homogenized for 20 min at 2.3%. It was mechanically disintegrated using an Ultra Turrax mixer (IKA, D125 Basic) for 20 min to obtain a uniform hydrogel. Then 35 mg of the cellulose hydrogel with $Ac_2O$ was applied over a Teflon mold (60 mm×140 mm) by a rod coating setup, K101 Control Coater, RK Print Coat Instruments Ltd, Herts, UK. 1.5% of $Ac_2O$ of the dry weight of HT BKHWP was added to the hydrogel mixture and was mixed for a few seconds. These NFC—HT BKHWP films without any further pretreatment were dried at 23° C. and 50% RH for 24 h. The mechanical performance of the films made by different ratio between HT BKHW pulp and NFC (30:70, 50:50, 60:40, 70:30) was evaluated.

Analysis

Tensile testing of the cellulose films was carried out at 23° C. and 50% RH using an Instron 4204 Universal Tensile Tester equipped with a 50 N load cell, a gauge length of 40 mm and a cross-head speed of 1 mm/min. The film specimens were 10 mm wide and 50 mm long and they were equilibrated for at least three hours at RH 50%, before mechanical testing. For film imaging, Scanning electron microscope (SEM) was used with magnifications 10 300× and 35 490× (Zeiss Sigma VP Field-Emission Scanning Electron Microscope (FE-SEM)). The operating voltage was 3 kV and the working distance approximately 2.5 mm. Prior to the imaging, the sample was sputtered by gold-palladium.

A relative humidity (RH) of 50% and a temperature of 25° C. were maintained during the mechanical testing measurements. The film thickness was estimated by a thickness gauge under a low and constant pressure, according to the international standard regarding thickness of paper and board (ISO 534). RH conditions during the thickness measurement and mechanical testing were maintained (RH 50% and 25° C.). The film densities were calculated from the volumes and weights of the dry films after conditioning at 23° C. and 50% RH. This apparent density measurement was repeated at least three times for each sample. The moisture contents of conditioned films were calculated from the weight before and after heating at 100° C. for 3 h.

Results and Discussion

Adding insoluble mineral filler such as $CaCO_3$ improves the bonding capacity of the fibers, however it can simultaneously enhance the non-bonding area between the fillers and the cellulose. The present work provides a method to improve the mechanical properties of cellulose films by crosslinking with $Ca^{2+}$ cations and increase the bonding area between the cellulose fibrils and the fillers. In this procedure, adding $Ac_2O$ led to release $Ca^{2+}$ cations and to react with the carboxyl groups on NFC. 1.5% $Ac_2O$ of the dry weight of the HT BHKP was optimized to prevent the agglomeration of the cellulose gels after crosslinking.

The mixture of PCC-fiber-NFC networks could enhance the strength of formed composite materials. It was possible to produce cellulose films made by the combination of PCC-HT BKHWP and NFC. Indeed, the hydrogen-bonding network created by the longer cellulose fibers in the mixture with the shorter cellulose fibrils could produce stiffer cellulose films. The shorter fibrils are able to pack closer together, preventing substantial weakening of the bonds. Moreover, the longer cellulose fibers enhance the flexibility of the final cellulose products. The hemicellulose and lignin, however, do not affect significantly the tensile strength of the product.

Figure 5:
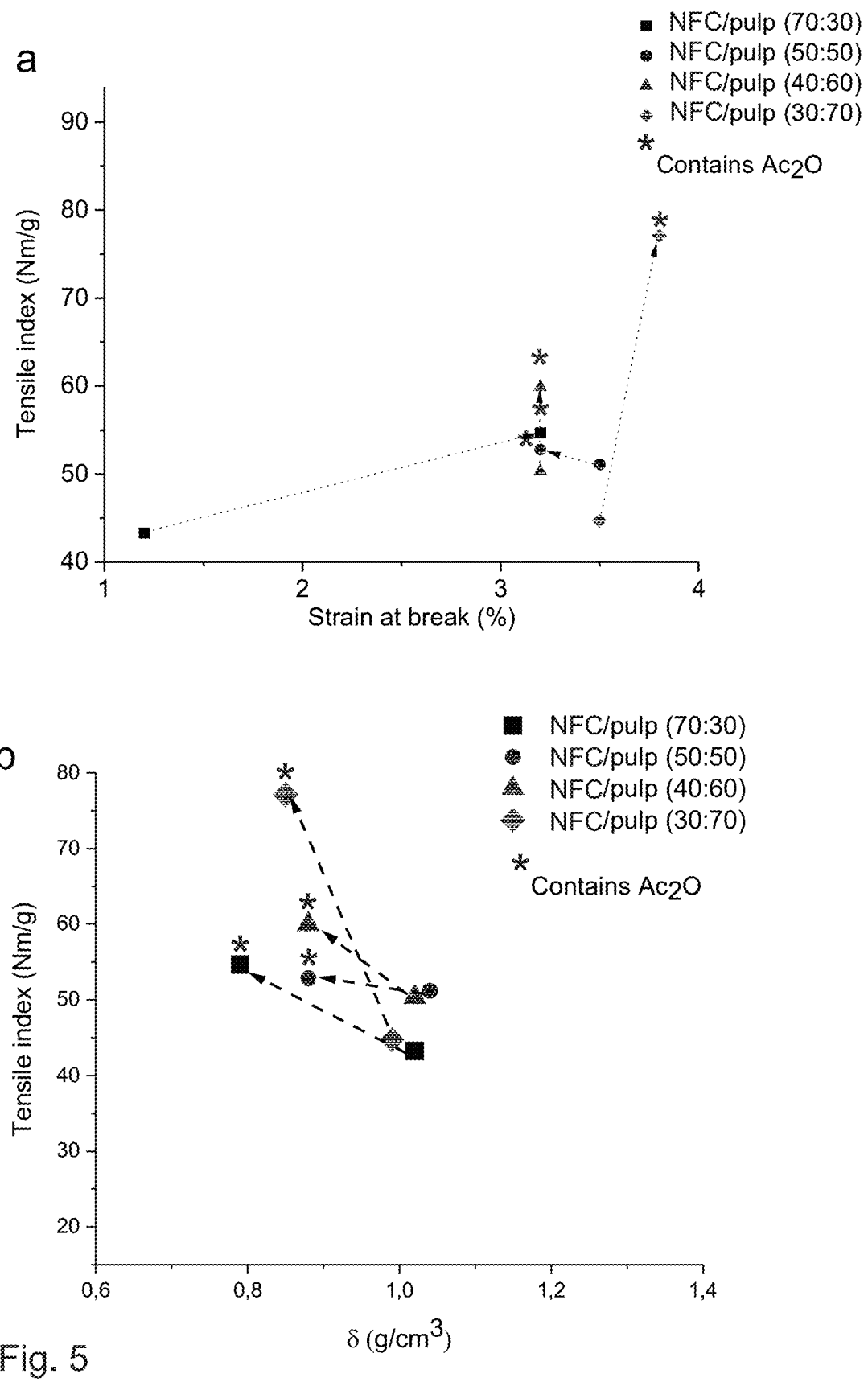
FIG. 5 shows tensile index against strain at break (a) and density (b) for cellulose films, prepared by different molar ratio of PCC-HT BHKP and NFC at 23° C. and 50% RH.

It was found out that using different ratios between HT BHKP and oxidized NFC influences the final cellulose products. The results of the tensile strength properties (tensile strength, strain-at-break, young's modulus) of the cellulose films are presented in FIG. 5. Table 4 shows that the cellulose films with 70% of PCC-HT BKHWP and 30% of NFC have highest tensile index and break-at-strain. This was because its uniform cellulose hydrogel of PCC-HT BHKP/NFC (70:30) may release more calcium cations to crosslink with the carboxyl groups compared to the cellulose hydrogel that contained less 70% PCC-HT BHKP.

The even cellulose films with higher quality were constructed by the combination of NFC with HT BHKP in different ratios (Table 4). It was also noted that films containing more than 70% of NFC had remarkable shrinkage and were brittle after drying. It was not possible to measure the mechanical properties of those low quality films. The molarity of the added $Ac_2O$ was varied depending on the dry content of cellulose fibers that contained $CaCO_3$. Those samples with 70% of cellulose fibers (PCC-HT BHKP) required 8 µl of $Ac_2O$.

Thin layer of the cellulose mixture gel with $Ac_2O$ dried for 24 h in 50% RH and in the room temperature (RT) to obtain the cellulose films with homogenous appearance and uniform thickness. During drying the cellulose films, released calcium cations can bond with carboxylate groups of the NFC.

Adding $Ac_2O$ led to reduce pH via the acidic hydrolysis from 7.3 to 4.8 during 15 min. Then under this mild acidic condition, it created bond between the calcium cations with the carboxyl groups on the NFC, improved the mechanical properties of the cellulose films. Indeed, cellulose films were prepared based on an ionic cross-linkage interaction between the positively charged calcium cations and the negatively charged carboxylate groups on the NFC. However, the modulus unchanged after adding $Ac_2O$, but the strength and strain in break were developed. The maximum strength and toughness of the cellulose films were caused by the cross-linking process which it enhanced the creation of bridges between the cellulose fibers.

Figure 6:
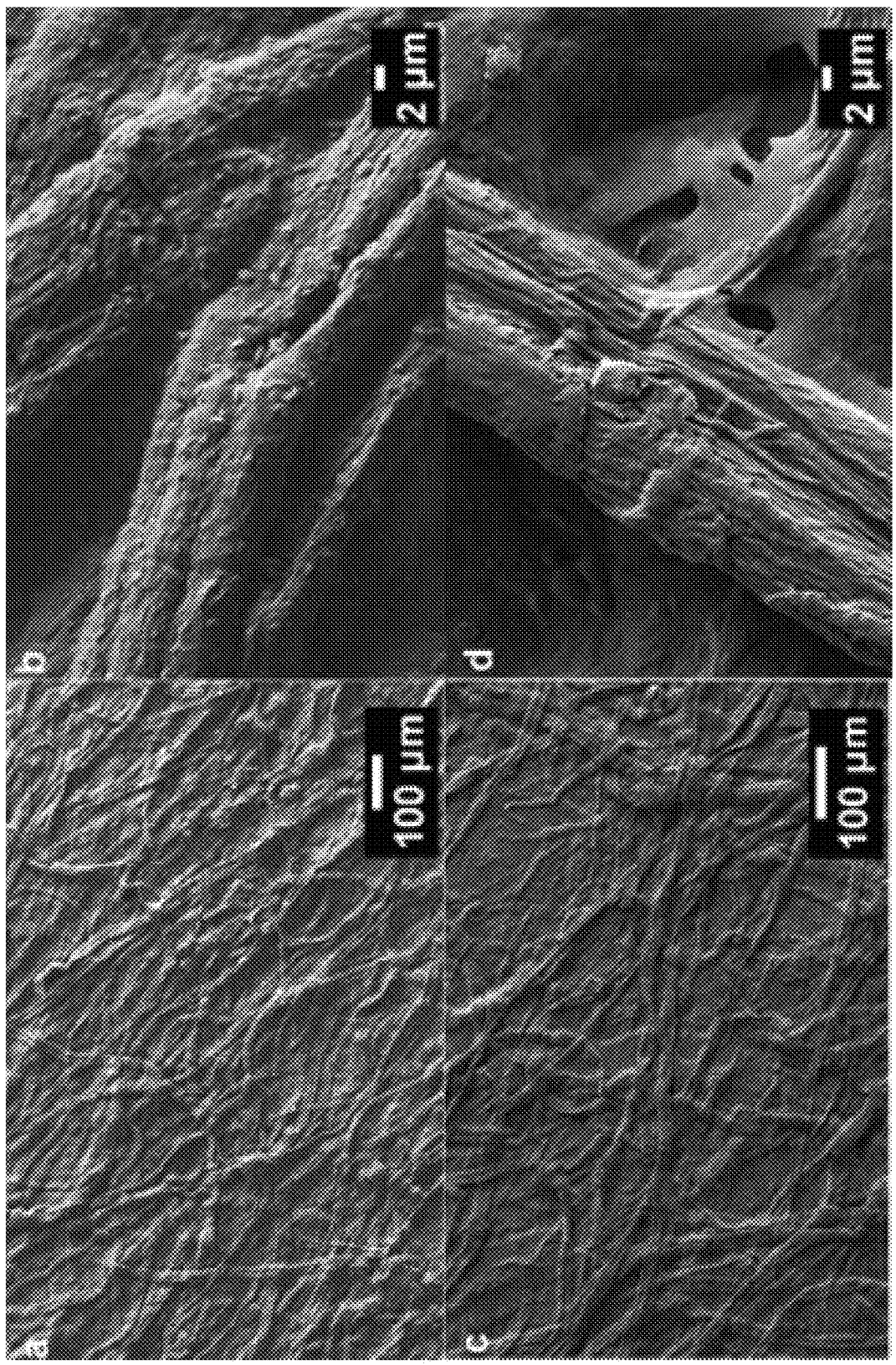
FIG. 6 shows SEM images of the surface of the cellulose films made by 70% of PCC-HT BHKP and 30% of NFC before (a, b) and after (c, d) dissolution of $CaCO_3$.
Figure 7:
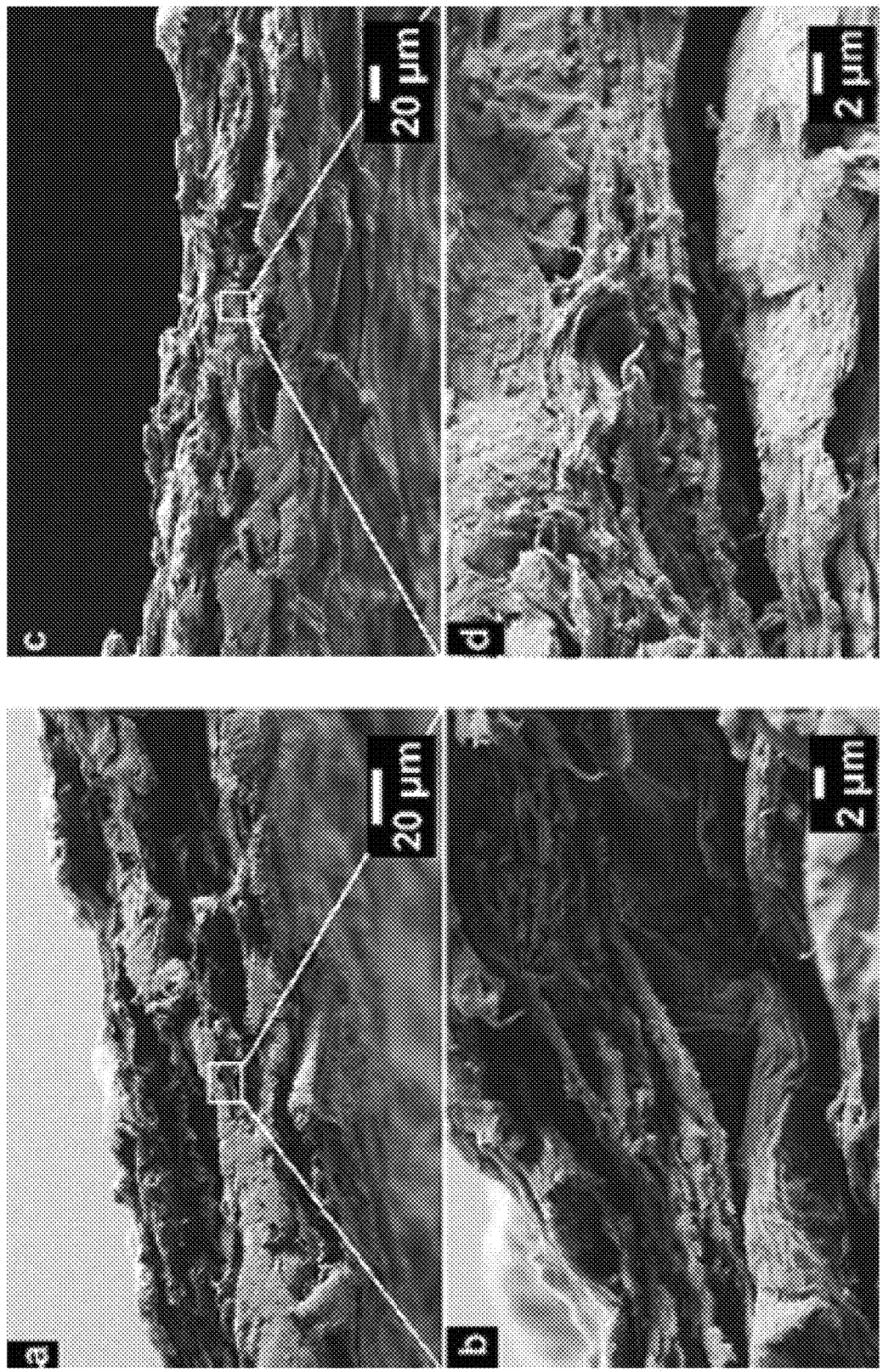
FIG. 7 shows SEM images of the freeze-fractured surface of cellulose films made by 70% of PCC-HT BHKP and 30% of NFC after addition of $Ac_2O$ before (a, b) and after (c, d) cross-linking treatment in different magnifications.

SEM images of the prepared cellulose films surface (FIGS. 6a and b) shows the microparticles of precipitated $CaCO_3$ on the surface of the fiber before addition of $Ac_2O$ in different magnifications, whereas these $CaCO_3$ microparticles disappeared in presence of $Ac_2O$ (FIGS. 6c and d). The images of cross sections shows the layered structure of the cellulose films which do not have any specific difference (FIG. 7).

TABLE 4

Mechanical properties of the cellulose films, their moisture contents and densities at 23° C. and 50 RH.

| Samples | Tensile index (Nm/g) | Strain (%) | Young's modulus (GPa) | Moisture content, % | Thickness (µm) | Density (g/cm³) |
| --- | --- | --- | --- | --- | --- | --- |
| NFC/pulp (70:30) | 43.3 ± 4.5 | 1.2 ± 0.1 | 5.8 ± 0.7 | 7.1 ± 0.7 | 100 ± 8.5 | 1.02 ± 0.0 |
| NFC/pulp (70:30) - $Ac_2O$ | 54.7 ± 6.4 | 3.2 ± 0.1 | 5.5 ± 1.2 | 9.1 ± 0.6 | 89 ± 9.5 | 0.79 ± 0.1 |
| NFC/pulp (50:50) | 51,1 ± 1.3 | 3.5 ± 0.1 | 5.2 ± 0.4 | 7.6 ± 0.5 | 113 ± 4.5 | 1.04 ± 0.1 |
| NFC/pulp (50:50) - $Ac_2O$ | 52.8 ± 9.8 | 3.2 ± 0.3 | 3.4 ± 0.9 | 8.1 ± 1.1 | 145 ± 4.4 | 0.88 ± 0.0 |
| NFC/pulp (40:60) | 50.3 ± 4.5 | 3.2 ± 0.1 | 3.4 ± 0.9 | 7.9 ± 0.8 | 107 ± 8 | 1.02 ± 0.1 |
| NFC/pulp (40:60) - $Ac_2O$ | 59.9 ± 11.2 | 3.2 ± 0.8 | 3.9 ± 0.6 | 7.5 ± 1.15 | 133 ± 1 | 0.88 ± 0.1 |
| NFC/pulp (30:70) | 44.7 ± 6.0 | 3.5 ± 0.8 | 2.5 ± 0.0 | 6.7 ± 1.3 | 137 ± 8 | 0.99 ± 0.23 |
| NFC/pulp (30:70) - $Ac_2O$ | 77.1 ± 16.0 | 3.8 ± 0.3 | 3.5 ± 1.7 | 7.8 ± 2.5 | 145 ± 9 | 0.85 ± 0.1 |

Density of cellulose films decreased after bond formation between calcium cations and carboxylate groups on the surface of NFC (Table 4). However, the modulus and moisture contents were unchanged after adding $Ac_2O$.

The films which were prepared from the 30% PCC-HT BKHW pulp and 70% of NFC without addition of $Ac_2O$, showed lower mechanical performance than the other samples. In contrast, the cellulose films with 70% of PCC- HT BKHW pulp and 30% of NFC after addition of Ac$_2$O had highest tensile strength, strain-to-failure values of 77 Nm/g and 3.8%, respectively. Therefore, 70:30 of PCC-HT BKHWP/NFC is the best ratios for producing the stiff and flexible cellulose films in presence of Ac$_2$O.

Overall, the results presented that the tensile index and breaking strain enhanced after cross-linking treatment. Moreover, the density of the cellulose films decreased after bond formation between calcium cations and carboxyl groups on the cellulose content. The molar ratios between PCC-HT BKHWP and NFC significantly influences the stiffness of the cellulose films. These observations point to the fact that the fibril aggregation and floc formation can be controlled under the optimized acidic condition. It was found out that the mechanical properties of the cellulose film with 70:30 of PCC-HT BKHWP/NFC, after cross-linking with calcium cations, were significantly increased compared to the non-cross-linked cellulose films. The cross-linking treatment after adding Ac$_2$O as presented herein is an efficient approach to produce strong fiber networks without using additive or plasticizer and just in few second.

Conclusion

The efficient green method with interaction of the anionic carboxylic groups of cellulose with divalent cations can be used to improve the mechanical properties of the cellulose films without flock formation. The result presented that 70% of PCC-HT BKHWP in combination with 30% of NFC in presence of Ac$_2$O showed the highest tensile index 77 Nm/g and strains-to-failure of 3.8 at 23° C. and 50% RH. It has been shown by SEM images that 5% of precipitate CaCO$_3$ on the surface of the cellulose fibers dissolved after acid hydrolysis. Thus, released calcium cations after acid hydrolysis process were able to react with the carboxylate groups presents on NFC surfaces. This mechanical improvement can be explained by formation of inter-fibrillar cross-linkages with calcium cations in the cellulose films. 8 µl of Ac$_2$O was added to the PCC-HT BKHWP/NFC (70:30) to avoid aggregation during the sheet preparation. Cellulose films constructed by more than 70% of NFC or 70% of PCC-HT BKHWP contained wrinkle and uneven structure, respectively. Fibers contents affect either density and improvement of the mechanical properties of the cellulose films. Because it was observed that 16.4% of the density of the non-crosslinked cellulose films was decreased after bond formation by the calcium cations. In packaging applications, it is important to develop high strength at relatively low sheet densities.

Example 3: Moisture Content at Ambient Conditions

Figure 9:
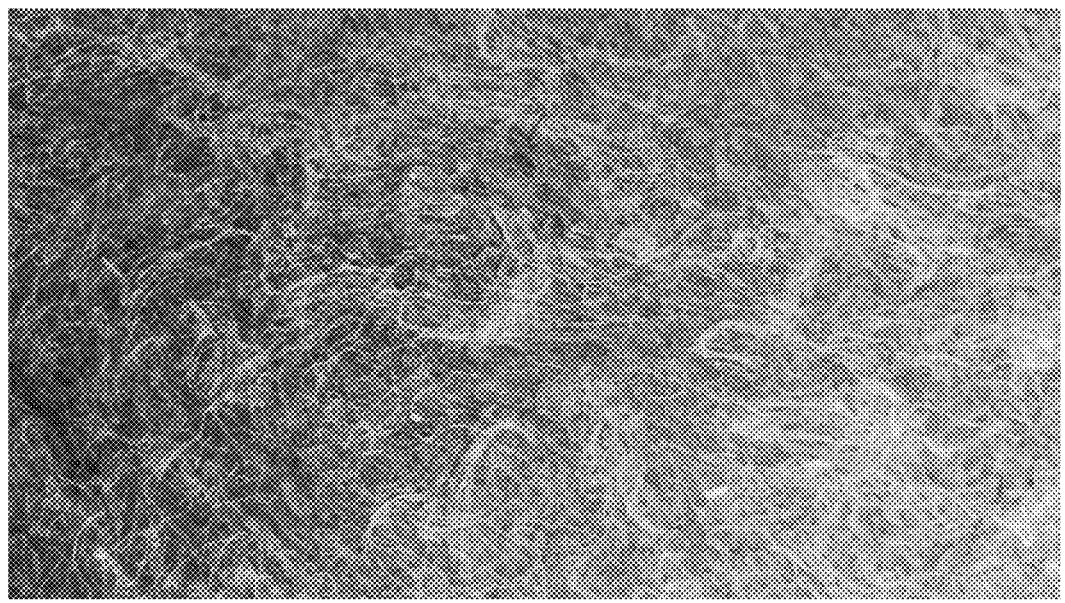
FIG. 9 shows a sample of a thick film of oxidized NFC and cut flax fibers; treated with aqueous $CaCl_2$).

Moisture contents of two flexible samples presented in FIGS. 8 and 9 were determined after keeping the samples for one week at ambient conditions exposed in an office at normal room temperature. The sample shown in FIG. 8 was a thin film of oxidized NFC and pulp treated with aqueous CaCl$_2$) and dried at 50° C. It was determined having a final moisture content of 16.4% after the exposure. A sample was a thick film of oxidized NFC and cut flax fibers treated with aqueous CaCl$_2$) and then dried at 50° C. It was determined having a moisture content of 12.9% after the exposure.

The invention claimed is:

1. A product comprising a layer comprising anionically modified nanofibrillar cellulose having a carboxylic acid content in the range of 0.5-2.0 mmol COOH/g pulp determined by conductometric titration, and multivalent cations, wherein the nanofibrillar cellulose is crosslinked by the multivalent cations, wherein the product has a moisture content in the range of 0-20% (w/w), and wherein the product has an elongation of 3.2% or higher.

2. The product of claim 1, wherein the product has a moisture content in the range of 5-20% (w/w).

3. The product of claim 1, wherein the product has a density in the range of 0.8-1.2 g/cm$^3$.

4. The product of claim 1, wherein the product has a tensile index in the range of 28-95 Nm/g.

5. The product of claim 1, wherein the product is in a form of, or is incorporated in, a layer, a coating, a film, a sheet, a membrane, incorporated in a gauze, or is in a form of a filter, a paper, a cardboard, or a nonwoven.

6. The product of claim 1 comprising one or more therapeutic agent and/or one or more cosmetic agent(s).

7. The product of claim 1 obtained by a method comprising:
providing anionically modified nanofibrillar cellulose having a carboxylic acid content in the range of 0.5-2.0 mmol COOH/g pulp determined by conductometric titration,
forming the anionically modified nanofibrillar cellulose into a form of a product comprising a layer comprising nanofibrillar cellulose,
providing multivalent cations,
contacting the anionic nanofibrillar cellulose in the form of the product comprising a layer comprising nanofibrillar cellulose with the multivalent cations, and
allowing reacting for a period of time to obtain a product comprising a later comprising crosslinked nanofibrillar cellulose and dewatering the product comprising a later comprising crosslinked nanofibrillar cellulose product to a moisture content in the range of 0-20% (w/w).

8. The product of claim 1 comprising
the layer comprising the nanofibrillar cellulose, and
a layer of gauze or nonwoven.

9. The product of claim 1, wherein the nanofibrillar cellulose has a carboxylic acid content in the range of 0.6-1.4 mmol COOH/g determined by conductometric titration.

10. The product of claim 1, wherein the multivalent cations are selected from cations of calcium, magnesium, zinc, aluminum, gold, platinum and titanium.

11. A method for treating a patient, the method comprising
providing the nanofibrillar cellulose product of claim 1, and
applying the nanofibrillar cellulose product onto skin of the patient.

12. The product of claim 1, comprising 0.1-70% (w/w) of non-fibrillar fibers based on the dry weight of the total material.

13. A method for preparing a product comprising a layer comprising anionically modified nanofibrillar cellulose having a carboxylic acid content in the rang of 0.5-2.0 mmol COOH/g pulp determined by conductometric titration, and multivalent cations, wherein the nanofibrillar cellulose is crosslinked by the multivalent cations, wherein the product has a moisture content in the range of 0-20% (w/w), and wherein the product has an elongation of 3.2% or higher, the method comprising
providing anionically modified nanofibrillar cellulose having a carboxylic acid content in the range of 0.5-2.0 mmol COOH/g pulp determined by conductometric titration, forming the anionically modified nanofibrillar cellulose into a form of a product comprising a layer comprising nanofibrillar cellulose, providing multivalent cations, contacting the anionic nanofibrillar cellulose in the form of the product comprising a layer comprising nanofibrillar cellulose with the multivalent cations, and allowing reacting for a period of time to obtain a product comprising a layer comprising crosslinked nanofibrillar cellulose and dewatering the product comprising a layer comprising crosslinked nanofibrillar cellulose product to a moisture content in the range of 0-20% (w/w).

14. The method of claim 13, wherein the nanofibrillar cellulose has a carboxylic acid content in the range of 0.6-1.4 mmol COOH/g, determined by conductometric titration.

15. The method of claim 13, wherein the multivalent cations are provided as an aqueous solution.

16. The method of claim 13, wherein the multivalent cations are provided as insoluble salt, the method further comprising providing an acid-releasing compound, wherein the released acid is capable of solubilizing the multivalent cations and wherein the acid is arranged to be released as delayed release.

17. The method of claim 16, wherein the contacting the anionically modified nanofibrillar cellulose with the multivalent cations comprises forming a mixture of the nanofibrillar cellulose, the multivalent cations and the acid-releasing compound.

18. The method of claim 16, wherein the acid-releasing compound is selected from an anhydride and an ester.

19. The method of claim 13, comprising forming the nanofibrillar cellulose before crosslinking into a layer, a coating, a film, a sheet, or a membrane.

20. The method of claim 13 comprising forming the nanofibrillar cellulose before crosslinking into a layer or a coating in a multi-layer product.

21. The method of claim 13, wherein the nanofibrillar cellulose has an average diameter of a fibril in the range of 1-200 nm and/or, when dispersed in water, the nanofibrillar cellulose provides a zero shear viscosity in the range of 1000-100000 Pa s, and a yield stress in the range of 1-50 Pa, determined by rotational rheometer at a consistency of 0.5% (w/w) by weight in aqueous medium.

22. The method of claim 13, wherein the multivalent cations are selected from cations of calcium, magnesium, zinc, aluminum, gold, platinum and titanium.

23. The method of claim 13, wherein the multi-layer product comprises a layer of gauze or nonwoven.

24. The method of claim 13, comprising providing a gauze and incorporating the nanofibrillar cellulose to the gauze before crosslinking.

25. The method of claim 24, wherein the incorporating comprises impregnating the gauze with the nanofibrillar cellulose.

* * * * *